United States Patent
Braun et al.

(10) Patent No.: US 8,400,277 B2
(45) Date of Patent: Mar. 19, 2013

(54) METHODS, APPARATUSES, AND COMPUTER PROGRAM PRODUCTS FOR MONITORING A TRANSFER OF FLUID BETWEEN A SYRINGE AND A FLUID RESERVOIR

(75) Inventors: Patrick Joseph Braun, Pittsburgh, PA (US); Shawn T. Greyshock, Tarentum, PA (US)

(73) Assignee: McKesson Automation Inc., Cranberry, PA (US)

( * ) Notice: Subject to any disclaimer, the term of this patent is extended or adjusted under 35 U.S.C. 154(b) by 919 days.

(21) Appl. No.: 12/414,054

(22) Filed: Mar. 30, 2009

(65) Prior Publication Data

US 2010/0245056 A1   Sep. 30, 2010

(51) Int. Cl.
*G08B 21/00* (2006.01)
(52) U.S. Cl. ............. 340/10.42; 340/10.4; 340/572.1; 340/572.8; 600/300; 600/301; 604/187
(58) Field of Classification Search ............ 340/10, 340/572; 600/300, 301; 604/187; 141/27; 700/231
See application file for complete search history.

(56) References Cited

U.S. PATENT DOCUMENTS

| | | | |
|---|---|---|---|
| 4,717,042 A | 1/1988 | McLaughlin | |
| 4,785,969 A | 11/1988 | McLaughlin | |
| 4,847,764 A | 7/1989 | Halvorson | |
| 5,003,296 A | 3/1991 | Lee | |
| 5,014,875 A | 5/1991 | McLaughlin et al. | |
| 5,190,185 A | 3/1993 | Blechl | |
| 5,314,243 A | 5/1994 | McDonald et al. | |
| 5,346,297 A | 9/1994 | Colson, Jr. et al. | |
| 5,377,864 A | 1/1995 | Blechl et al. | |
| 5,405,048 A | 4/1995 | Rogers et al. | |
| 5,431,299 A | 7/1995 | Brewer et al. | |
| 5,460,294 A | 10/1995 | Williams | |
| 5,468,110 A | 11/1995 | McDonald et al. | |
| 5,480,062 A | 1/1996 | Rogers et al. | |
| 5,520,450 A | 5/1996 | Colson, Jr. et al. | |
| 5,564,803 A | 10/1996 | McDonald et al. | |
| 5,593,267 A | 1/1997 | McDonald et al. | |
| 5,661,978 A | 9/1997 | Holmes et al. | |

(Continued)

OTHER PUBLICATIONS

SP Central; "*Pharmacy Management System & Workflow System;*" ScriptPro®, Pharmacy Automation; www.scriptpro.com; Mar. 30, 2009 http://www.scriptpro.com/products/SPC_PMS_Workflow_brochure_single_pgs.pdf.

(Continued)

*Primary Examiner* — Wayne Young
*Assistant Examiner* — Mark Rushing
(74) *Attorney, Agent, or Firm* — Alston & Bird LLP

(57) ABSTRACT

A method, apparatus, and computer program product are provided for monitoring a transfer of fluid between a syringe and a fluid reservoir. A syringe may include a chamber for holding fluid transferred between the syringe and a fluid reservoir, a distal end comprising a point of attachment for a needle enabling transfer of fluid between the syringe and the fluid reservoir, and a first signaling tag carried by the syringe. The first signaling tag may be positioned to enable the first signaling tag to come within a sufficient proximity of a second signaling tag carried by the fluid reservoir to trigger a state of a signal emitted by at least one of the first signaling tag or second signaling tag to change when the needle is inserted through a membrane of the fluid reservoir.

23 Claims, 14 Drawing Sheets

U.S. PATENT DOCUMENTS

| | | | |
|---|---|---|---|
| D384,578 S | 10/1997 | Wangu et al. |
| 5,713,485 A | 2/1998 | Liff et al. |
| 5,716,114 A | 2/1998 | Holmes et al. |
| 5,745,366 A | 4/1998 | Higham et al. |
| 5,761,877 A | 6/1998 | Quandt |
| 5,797,515 A | 8/1998 | Liff et al. |
| 5,805,456 A | 9/1998 | Higham et al. |
| 5,842,976 A | 12/1998 | Williamson |
| 5,878,885 A | 3/1999 | Wangu et al. |
| 5,880,443 A | 3/1999 | McDonald et al. |
| 5,883,806 A | 3/1999 | Meador et al. |
| 5,893,697 A | 4/1999 | Zini et al. |
| 5,905,653 A | 5/1999 | Higham et al. |
| 5,912,818 A | 6/1999 | McGrady et al. |
| 5,927,540 A | 7/1999 | Godlewski |
| 5,940,306 A | 8/1999 | Gardner et al. |
| 5,971,593 A | 10/1999 | McGrady |
| 6,003,006 A | 12/1999 | Colella et al. |
| 6,011,999 A | 1/2000 | Holmes |
| 6,021,392 A | 2/2000 | Lester et al. |
| 6,039,467 A | 3/2000 | Holmes |
| 6,065,819 A | 5/2000 | Holmes et al. |
| 6,068,156 A | 5/2000 | Liff et al. |
| 6,109,774 A | 8/2000 | Holmes et al. |
| 6,112,502 A | 9/2000 | Frederick et al. |
| 6,116,461 A | 9/2000 | Broadfield et al. |
| 6,151,536 A | 11/2000 | Arnold et al. |
| 6,170,230 B1 | 1/2001 | Chudy et al. |
| 6,176,392 B1 | 1/2001 | William et al. |
| 6,189,727 B1 | 2/2001 | Shoenfeld |
| 6,223,934 B1 | 5/2001 | Shoenfeld |
| 6,256,967 B1 | 7/2001 | Hebron et al. |
| 6,283,322 B1 | 9/2001 | Liff et al. |
| 6,285,285 B1 | 9/2001 | Mongrenier |
| 6,289,656 B1 | 9/2001 | Wangu et al. |
| 6,337,631 B1 | 1/2002 | Pai et al. |
| 6,338,007 B1 | 1/2002 | Broadfield et al. |
| 6,339,732 B1 | 1/2002 | Phoon et al. |
| 6,361,263 B1 | 3/2002 | Dewey et al. |
| 6,370,841 B1 | 4/2002 | Chudy et al. |
| 6,449,927 B2 | 9/2002 | Hebron et al. |
| 6,471,089 B2 | 10/2002 | Liff et al. |
| 6,497,342 B2 | 12/2002 | Zhang et al. |
| 6,499,270 B2 | 12/2002 | Peroni et al. |
| 6,532,399 B2 | 3/2003 | Mase |
| 6,564,121 B1 | 5/2003 | Wallace et al. |
| 6,581,798 B2 | 6/2003 | Liff et al. |
| 6,609,047 B1 | 8/2003 | Lipps |
| 6,611,733 B2 | 8/2003 | De La Huerga |
| 6,625,952 B1 | 9/2003 | Chudy et al. |
| 6,640,159 B2 | 10/2003 | Holmes et al. |
| 6,650,964 B2 | 11/2003 | Spano, Jr. et al. |
| 6,671,579 B2 | 12/2003 | Spano, Jr. et al. |
| 6,681,149 B2 | 1/2004 | William et al. |
| 6,690,280 B2 | 2/2004 | Citrenbaum et al. |
| 6,742,671 B2 | 6/2004 | Hebron et al. |
| 6,755,931 B2 | 6/2004 | Vollm et al. |
| 6,760,643 B2 | 7/2004 | Lipps |
| 6,776,304 B2 | 8/2004 | Liff et al. |
| 6,785,589 B2 | 8/2004 | Eggenberger et al. |
| 6,790,198 B1 | 9/2004 | White et al. |
| 6,814,254 B2 | 11/2004 | Liff et al. |
| 6,814,255 B2 | 11/2004 | Liff et al. |
| 6,847,861 B2 | 1/2005 | Lunak et al. |
| 6,874,684 B1 | 4/2005 | Denenberg et al. |
| 6,892,780 B2 | 5/2005 | Vollm et al. |
| 6,895,304 B2 | 5/2005 | Spano, Jr. et al. |
| 6,963,791 B1 | 11/2005 | Frederick et al. |
| 6,975,922 B2 | 12/2005 | Duncan et al. |
| 6,985,797 B2 | 1/2006 | Spano, Jr. et al. |
| 6,989,796 B2 | 1/2006 | Rahim |
| 6,996,455 B2 | 2/2006 | Eggenberger et al. |
| 7,010,389 B2 | 3/2006 | Lunak et al. |
| 7,014,063 B2 | 3/2006 | Shows et al. |
| 7,016,766 B2 | 3/2006 | William et al. |
| 7,040,504 B2 | 5/2006 | Broadfield et al. |
| 7,052,097 B2 | 5/2006 | Meek, Jr. et al. |
| 7,072,737 B2 | 7/2006 | Lunak et al. |
| 7,072,855 B1 | 7/2006 | Godlewski et al. |
| 7,077,286 B2 | 7/2006 | Shows et al. |
| 7,085,621 B2 | 8/2006 | Spano, Jr. et al. |
| 7,092,796 B2 | 8/2006 | Vanderveen |
| 7,093,755 B2 | 8/2006 | Jordan et al. |
| 7,100,792 B2 | 9/2006 | Hunter et al. |
| 7,103,419 B2 | 9/2006 | Engleson et al. |
| 7,111,780 B2 | 9/2006 | Broussard et al. |
| 7,139,639 B2 | 11/2006 | Broussard et al. |
| 7,150,724 B2 | 12/2006 | Morris et al. |
| 7,171,277 B2 | 1/2007 | Engleson et al. |
| 7,218,231 B2 | 5/2007 | Higham |
| 7,228,198 B2 | 6/2007 | Vollm et al. |
| 7,249,688 B2 | 7/2007 | Hunter et al. |
| 7,348,884 B2 | 3/2008 | Higham |
| 7,417,729 B2 | 8/2008 | Greenwald |
| 7,419,133 B2 | 9/2008 | Clarke et al. |
| 7,426,425 B2 | 9/2008 | Meek, Jr. et al. |
| 7,554,449 B2 | 6/2009 | Higham |
| 7,571,024 B2 | 8/2009 | Duncan et al. |
| 7,588,167 B2 | 9/2009 | Hunter et al. |
| 7,596,427 B1 | 9/2009 | Frederick et al. |
| 7,783,383 B2 | 8/2010 | Eliuk et al. |
| 7,821,401 B2 | 10/2010 | Martin et al. |
| 7,956,751 B2 | 6/2011 | Lenevez |
| 2002/0188259 A1* | 12/2002 | Hickle et al. ............ 604/189 |
| 2003/0117281 A1 | 6/2003 | Sriharto et al. |
| 2004/0061994 A1 | 4/2004 | Kerr et al. |
| 2005/0088305 A1 | 4/2005 | Greene et al. |
| 2006/0102718 A1 | 5/2006 | Kajino et al. |
| 2006/0108252 A1 | 5/2006 | Lax |
| 2006/0214864 A1 | 9/2006 | Rahim |
| 2006/0244599 A1 | 11/2006 | Taylor et al. |
| 2006/0264778 A1* | 11/2006 | Lim et al. ............... 600/576 |
| 2006/0289650 A1 | 12/2006 | Taylor et al. |
| 2007/0027577 A1 | 2/2007 | Lunak et al. |
| 2007/0229266 A1* | 10/2007 | Gibson ................. 340/572.1 |
| 2008/0051937 A1 | 2/2008 | Khan et al. |
| 2008/0195246 A1 | 8/2008 | Tribble et al. |
| 2008/0195416 A1 | 8/2008 | Tribble et al. |
| 2009/0043253 A1* | 2/2009 | Podaima ..................... 604/67 |
| 2009/0322545 A1* | 12/2009 | Gibson et al. ............ 340/618 |
| 2010/0265068 A1 | 10/2010 | Brackman et al. |

OTHER PUBLICATIONS

For Health Technologies, Inc.; "IntelliFill I.V.—Automates the Preparation of Small Volume I.V. Medication," http://www.fhtinc.com/pharmacy.html; Mar. 30, 2009.

For Health Technologies, Inc.; IntelliFlow™ Rx, I.V. Workflow Manager, http://www.fhtinc.com/FHZS_files/Blueprint_for_Your_I.V._Room%27s_Future.pdf, Mar. 30, 2009.

Valimed Medication Validation System; www.ValiMed.com; http://www.cdexinc.com/pages/valimedbrochure.pdf, Mar. 30, 2009.

Carmel Pharma AB; PhaSeal® Protects Those Who Care™; Göteborg, Sweden; www.carmelpharma.com Mar. 30, 2009.

Notice of Allowance for U.S. Appl. No. 12/342,749 dated Sep. 7, 2011.

Office Action for U.S. Appl. No. 12/342,749, dated Dec. 9, 2010.

Office Action for U.S. Appl. No. 12/342,749 dated May 11, 2011.

Notice of Allowance for U.S. Appl. No. 12/389,842 dated Mar. 15, 2011.

Response to Amendment for U.S. Appl. No. 12/389,842 dated May 3, 2011.

* cited by examiner

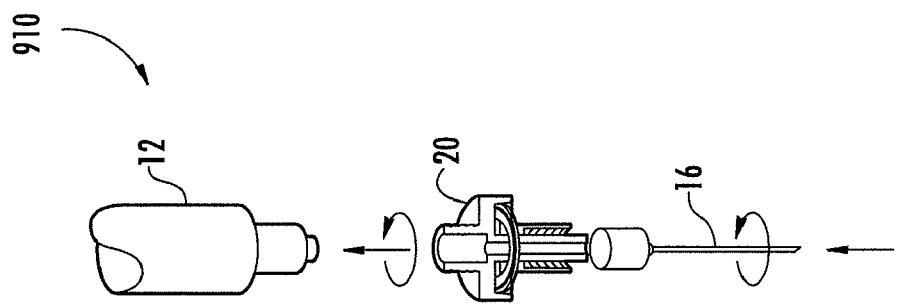
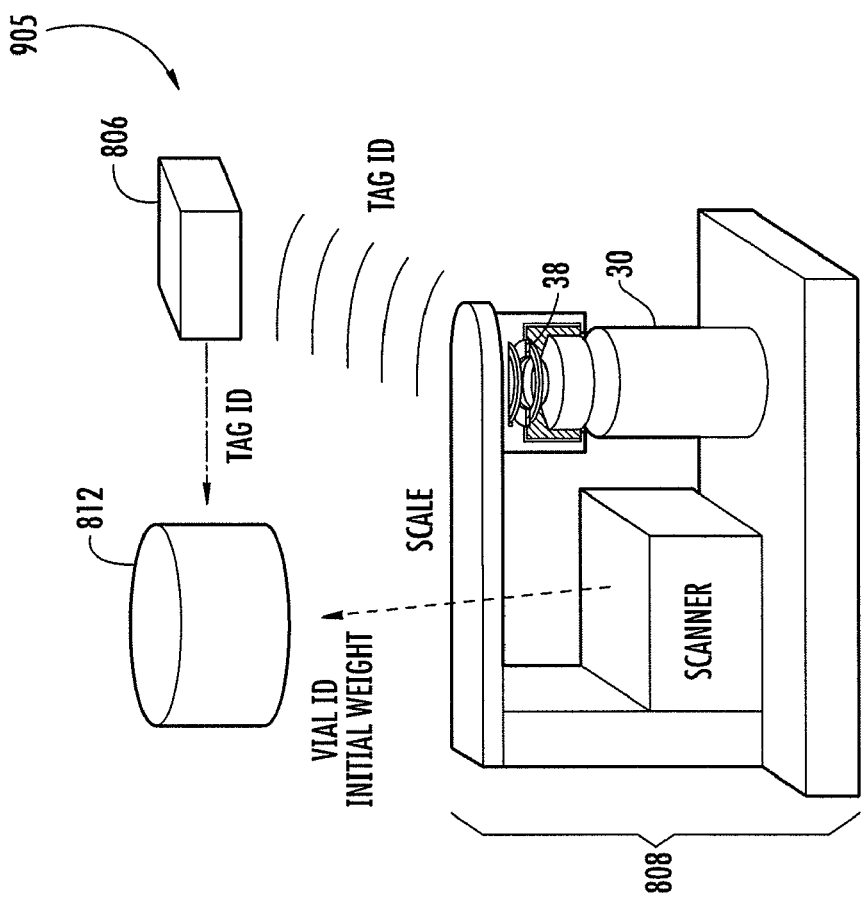
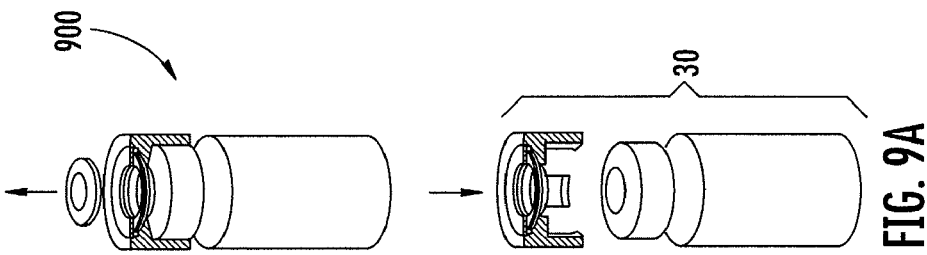

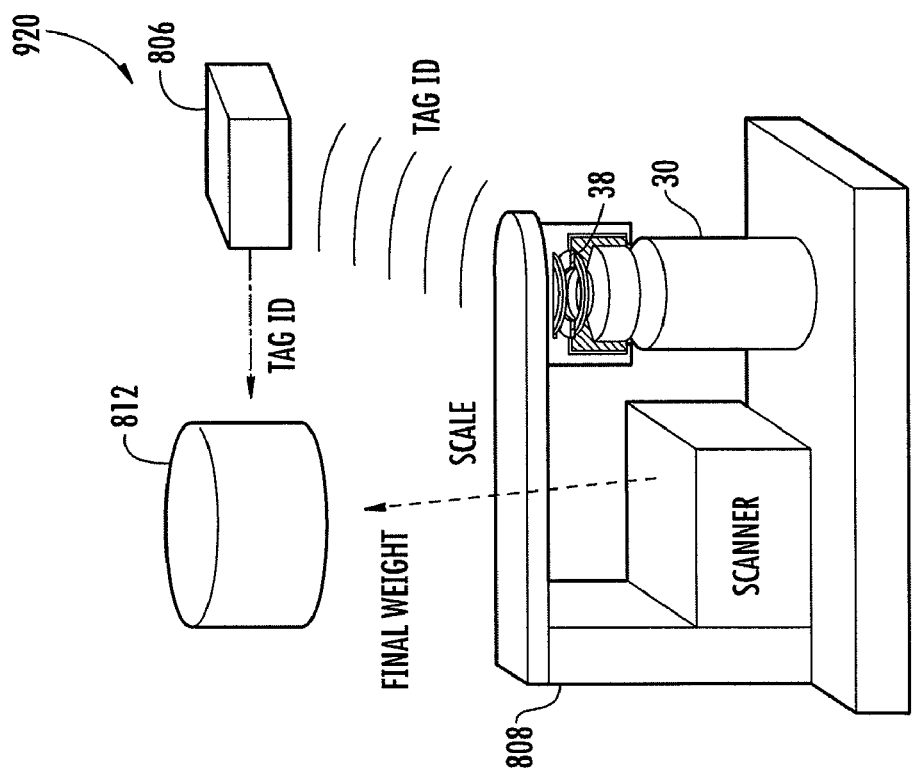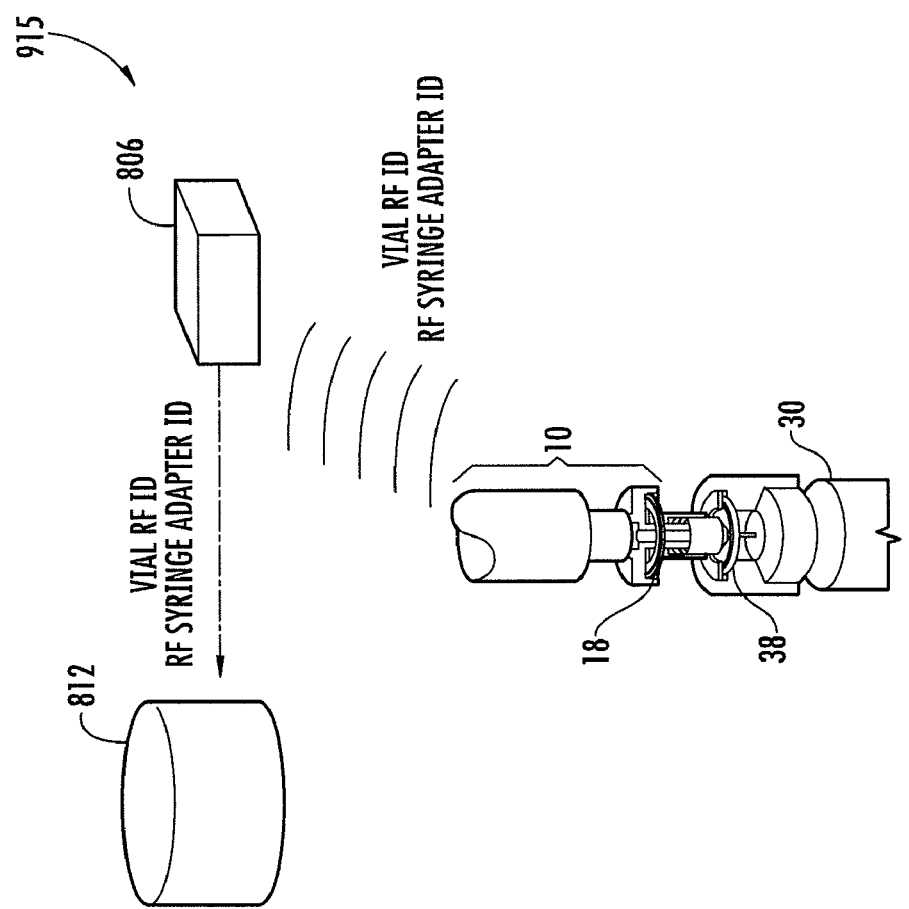

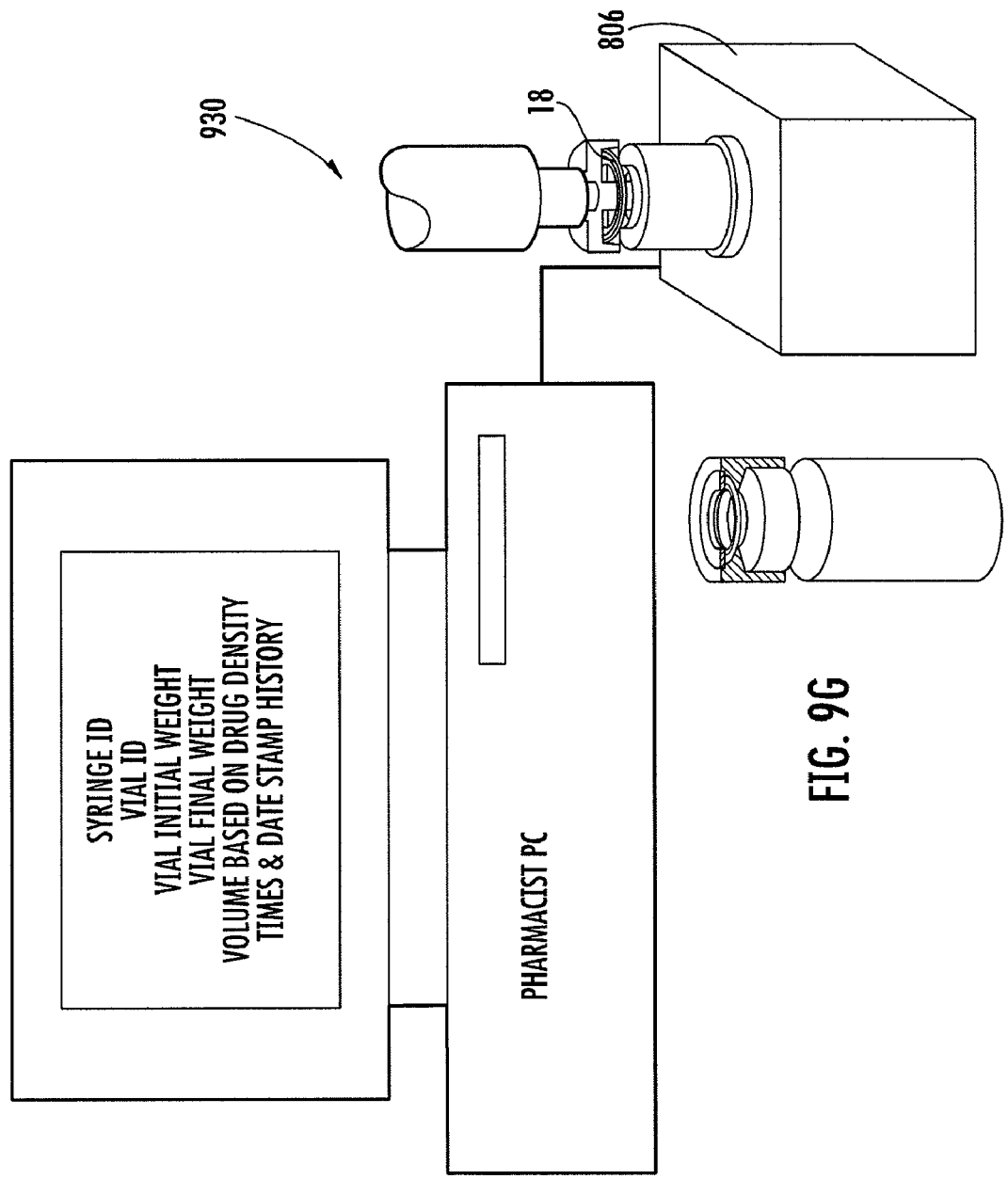

| ORDER NO. 6502 | PATIENT NAME: JOHN DOE | | | | PATIENT ID: 0657361 | | |
|---|---|---|---|---|---|---|---|
| WEIGHING OF COMPONENTS | | | PREPARATION HISTORY | | | | |
| SYRINGE/VIAL DRAW | | | | | | | |
| SYRINGE/IV BAG TRANSFER | | | | | | | |
| ENTRY | DATE | TIME STAMP | DRUG NAME | VIAL ID | VIAL WEIGHT | SYRINGE ID | IV BAG ID | IV BAG WEIGHT |
| 1 | 5/30/2008 | 9:15:25 | DRUG "A" | 222222220 | 17.00g | | 333333330 | 265.00g |
| 2 | 5/30/2008 | 9:16:55 | DRUG "A" | 222222220 | | 111111110 | | |
| 3 | 5/30/2008 | 9:17:25 | DRUG "A" | 222222220 | 12.00g | | | |
| 4 | 5/30/2008 | 9:17:55 | DRUG "A" | | | 111111110 | 333333330 | 269.90g |
| 5 | 5/30/2008 | 9:18:25 | DRUG "A" | 222222221 | 16.95g | | | |
| 6 | 5/30/2008 | 9:18:55 | DRUG "A" | 222222221 | | 111111110 | | |
| 7 | 5/30/2008 | 9:19:15 | DRUG "A" | 222222221 | 12.05g | | | |
| 8 | 5/30/2008 | 9:19:25 | DRUG "A" | | | 111111110 | 333333330 | 274.80 |
| 9 | 5/30/2008 | 9:20:25 | DRUG "B" | 555555550 | 7.05g | | | |
| 10 | 5/30/2008 | 9:21:55 | DRUG "B" | 555555550 | | 444444440 | | |
| 11 | 5/30/2008 | 9:22:15 | DRUG "B" | 555555550 | 6.00g | | | |
| 12 | 5/30/2008 | 9:22:55 | | | | 444444440 | 333333330 | 275.80 |
| 13 | 5/30/2008 | 9:23:15 | | | | | 333333330 | |

| | COMPONENT VOLUMES FOR DOSE | | |
|---|---|---|---|
| DRUG NAME | REQUIRED VOLUME | ACTUAL DRUG VOLUME | DEVIATION (ACCEPTABLE +/-5%) |
| DRUG "A" | 10.00 ml | 9.80 ml | 2% |
| DRUG "B" | 1.00 ml | 1.00 ml | 0.00% |
| IV BAG | 250 ml | | |

| | FINAL DOSE STATISTICS | | |
|---|---|---|---|
| REQUIRED VOLUME | ACTUAL VOLUME | DEVIATION (ACCEPTABLE +/-5%) | TOTAL PREP TIME |
| 261 ml | 260.80 ml | 0.10% | 0:07:50 |

FIG. 11

METHODS, APPARATUSES, AND COMPUTER PROGRAM PRODUCTS FOR MONITORING A TRANSFER OF FLUID BETWEEN A SYRINGE AND A FLUID RESERVOIR

TECHNOLOGICAL FIELD

Embodiments of the present invention relate generally to medical technology and, more particularly, relate to methods, apparatuses, and computer program products for monitoring a transfer of fluid between a syringe and a fluid reservoir.

BACKGROUND

Medications for administration to patients in medical facilities are often prepared in sterile facilities, such as intravenous (IV) medication rooms, in advance of administration to patients. Medical technicians often prepare the medications for administration based on instructions specified by a pharmacist or doctor responsible for preparation of the medication. In this regard, medical technicians may fill a syringe by transferring medication from a medicine vial to the syringe within a laminar hood. The filled syringe may either be delivered to medical personnel for injection into the patient or may be injected into an IV bag or IV line for administration to the patient intravenously. Sometimes, medical technicians are instructed to prepare IV bags by injecting multiple medications extracted from multiple medication vials into the IV bags in the sterile environment. The volume and type of each medication transferred into a syringe and/or injected into the IV bag may be specified in the instructions provided to the medical technician. In some instances, an order in which the medications are injected into the IV bag is critical and specified in the instructions.

As it is important to verify the prepared medications prior to actual administration to ensure that the patient receives the appropriate medications and volumes thereof, the preparation process is often verified by a pharmacist or other responsible medical personnel. However, due to sanitation concerns, logistical concerns, time concerns, and/or the like, it is often impractical to have a pharmacist directly observe or personally perform the preparation of syringes and IV bags. Accordingly, the process is frequently documented so that the pharmacist can verify the prepared syringes and IV bags prior to their administration to a patient.

Existing techniques for monitoring and documenting fluid transfer history are often tedious and may be extremely time consuming to implement. For example, photographic documentation of the process requires taking a photograph of each step of a process (e.g., a photograph showing a syringe pulled back to a specific volume while inserted into a specific medicine vial and then a photograph showing the same syringe inserted into a specific IV bag) and requires the technician to position each physical object so that the photograph captures a label or other identifying feature of the physical object to enable the pharmacist to verify the process. Thus photographic documentation may be quite time consuming and may further be unreliable if necessary identifying information is not fully captured in the documenting photographs.

In another existing technique known as the "pull-back method," a technician may prepare an IV mixture and pull all of the empty syringes back to reflect the volume of fluid that was injected into the IV bag using each respective syringe. The technician may then place the empty syringe(s) next to the vial(s) that were used to create the IV mixture so that the pharmacist may verify the contents of the IV bag. However, the pull-back method does not directly check contents or volumes during the preparation process, but rather the check is performed after preparing the IV mixture and introduces additional possibility of error, as the technician must attempt to recreate the injected volumes by pulling back the empty syringe(s) to reflect the volume(s) injected into the IV bag. Accordingly, the volumes provided for pharmacist verification may not be the actual volumes injected into the IV bag.

Accordingly, it would be advantageous to provide methods, apparatuses, and computer program products for more efficiently monitoring a transfer of fluid between a syringe and a fluid reservoir, such as a medication vial or IV bag.

BRIEF SUMMARY OF SOME EXAMPLES OF THE INVENTION

A method, apparatus, and computer program product are therefore provided for monitoring a transfer of fluid between a syringe and a fluid reservoir. In this regard, embodiments of the invention provide a syringe, such as may be used for transfer of fluid between a fluid reservoir and the syringe, which facilitates monitoring of the fluid transfer. Embodiments of the invention further provide a method and computer program product for monitoring a transfer of fluid between a syringe and fluid reservoir and generation of a database comprising a history of the transfer. The fluid transfer history may be used to verify preparation of medication dosages prior to administration and may reflect volumes of multiple medications transferred to a fluid reservoir, such as, for example, an IV bag.

In a first exemplary embodiment, a syringe is provided. The syringe may comprise a chamber for holding fluid transferred between the syringe and a fluid reservoir. The syringe may further comprise a distal end providing a point of attachment for a needle enabling transfer of fluid between the syringe and the fluid reservoir. The syringe may additionally comprise a first signaling tag carried by the syringe, such as proximate to the distal end. The first signaling tag may be positioned to enable the first signaling tag to come within a sufficient proximity of a second signaling tag carried by the fluid reservoir to trigger a state of a signal emitted by at least one of the first signaling tag or second signaling tag to change when the needle is inserted through a membrane of the fluid reservoir. The signal state change may be indicative of an associative relationship between the syringe and the fluid reservoir.

In another exemplary embodiment, a method for monitoring a transfer of fluid between a syringe and a fluid reservoir is provided. The syringe may comprise a distal end providing a point of attachment for a needle enabling the transfer of fluid. The fluid reservoir may comprise a membrane through which the needle is inserted for transferring fluid between the syringe and the fluid reservoir. The method may include detecting a change in state of a signal emitted by at least one of a first signaling tag carried by the syringe, such as proximate to the distal end of the syringe, or a second signaling tag carried by the fluid reservoir. The change in state of the signal may be triggered by the first and signaling tags coming into a sufficient proximity of one another when the needle is inserted through the membrane and may be indicative of an associative relationship between the syringe and the fluid reservoir. The method may further include determining an identity of the syringe based at least in part upon information carried by a signal emitted by the first signaling tag. The method may additionally include determining an identity of the fluid reservoir based at least in part upon information carried by a signal emitted by the second signaling tag. The method may also include associating the syringe with the fluid reservoir based at least in part upon the determined identities. The method may further include storing an entry reflecting the association between the syringe and the fluid reservoir in a database.

In another exemplary embodiment, a computer program product is provided. The computer program product is for a transfer of fluid between a syringe and a fluid reservoir. The syringe may comprise a distal end providing a point of attachment for a needle enabling the transfer of fluid. The fluid reservoir may comprise a membrane through which the needle is inserted for transferring fluid between the syringe and the fluid reservoir. The computer program product includes at least one computer-readable storage medium having computer-readable program instructions stored therein. The computer-readable program instructions may include a plurality of program instructions. Although in this summary, the program instructions are ordered, it will be appreciated that this summary is provided merely for purposes of example and the ordering is merely to facilitate summarizing the computer program product. The example ordering in no way limits the implementation of the associated computer program instructions. The first program instruction is for detecting a change in state of a signal emitted by at least one of a first signaling tag carried by the syringe or a second signaling tag carried by the fluid reservoir. The change in state of the signal may be triggered by the first and signaling tags coming into a sufficient proximity of one another when the needle is inserted through the membrane and may be indicative of an associative relationship between the syringe and the fluid reservoir. The second program instruction is for determining an identity of the syringe based at least in part upon information carried by a signal emitted by the first signaling tag. The third program instruction is for determining an identity of the fluid reservoir based at least in part upon information carried by a signal emitted by the second signaling tag. The fourth program instruction is for associating the syringe with the fluid based at least in part upon the determined identities. The fifth program instruction is for storing an entry reflecting the association between the syringe and the fluid reservoir in a database.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE DRAWING(S)

Having thus described embodiments of the invention in general terms, reference will now be made to the accompanying drawings, which are not necessarily drawn to scale, and wherein:

FIG. 9 illustrates a step-by-step process for monitoring a transfer of fluid from a medicine vial to a syringe according to an exemplary embodiment of the present invention;

Figure 10A:
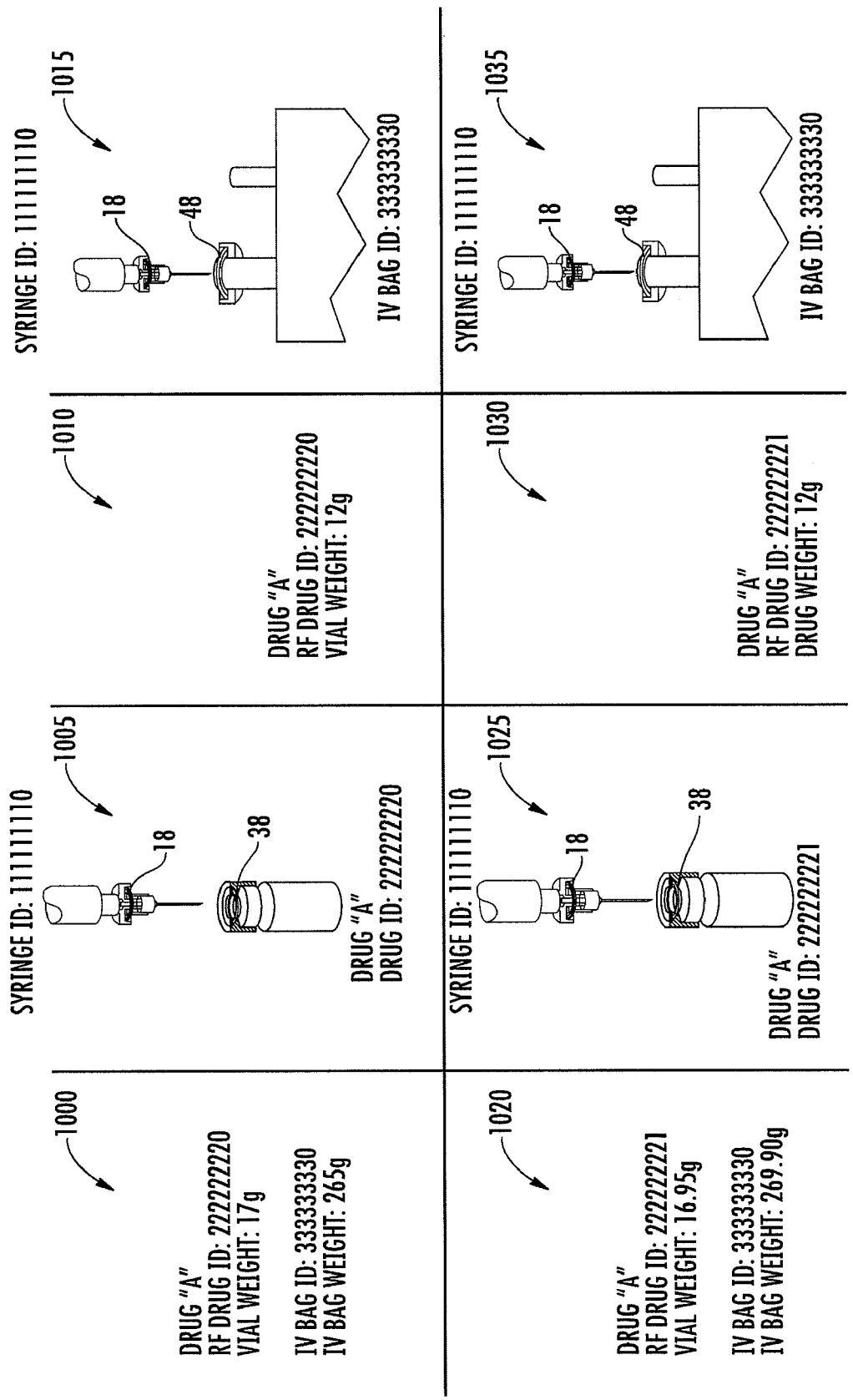
FIG. 10 illustrates a step-by-step process for monitoring a transfer of a plurality of medications to an IV bag according to an exemplary embodiment of the present invention.
Figure 10B:
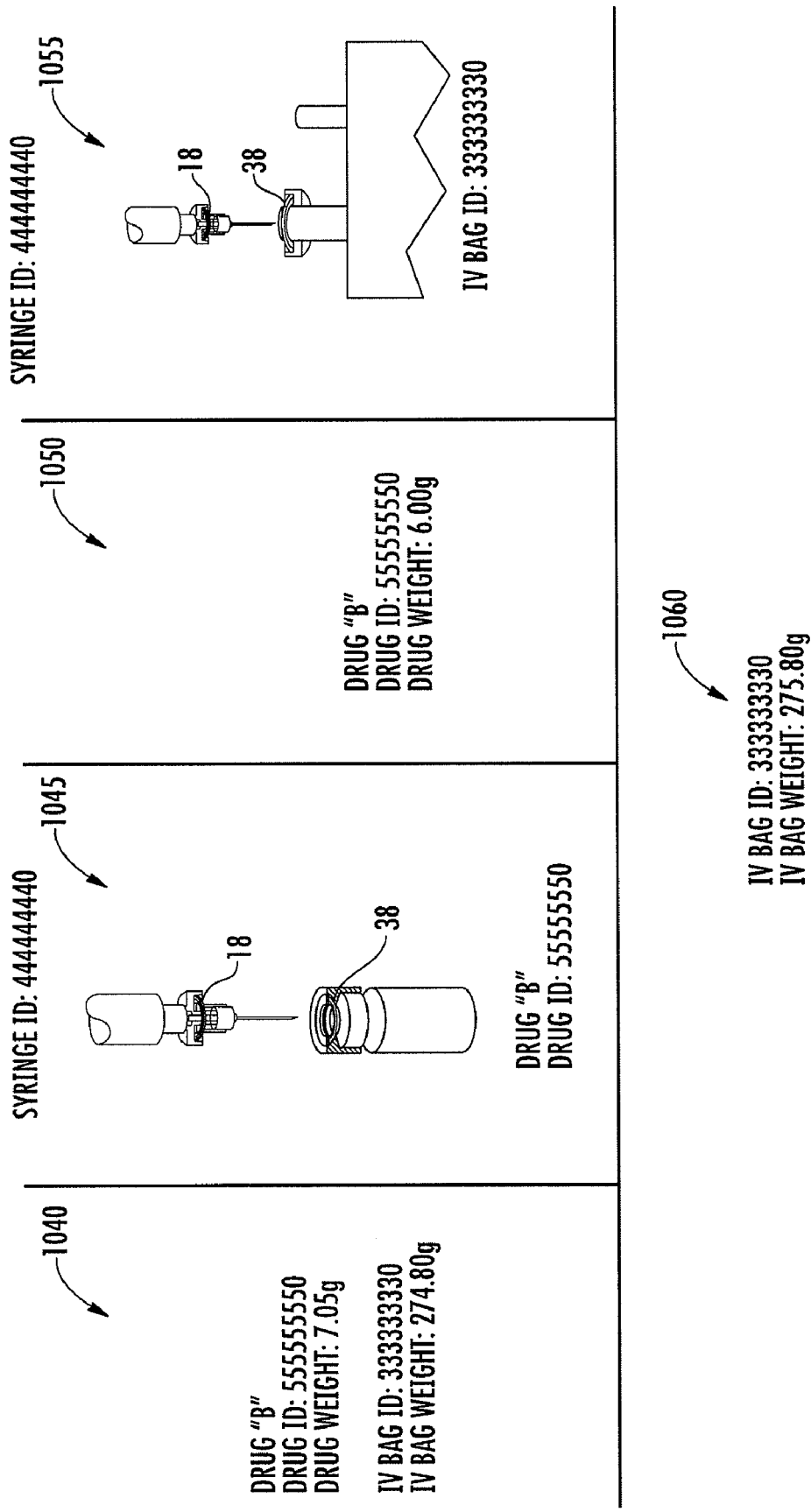
Figure 12:
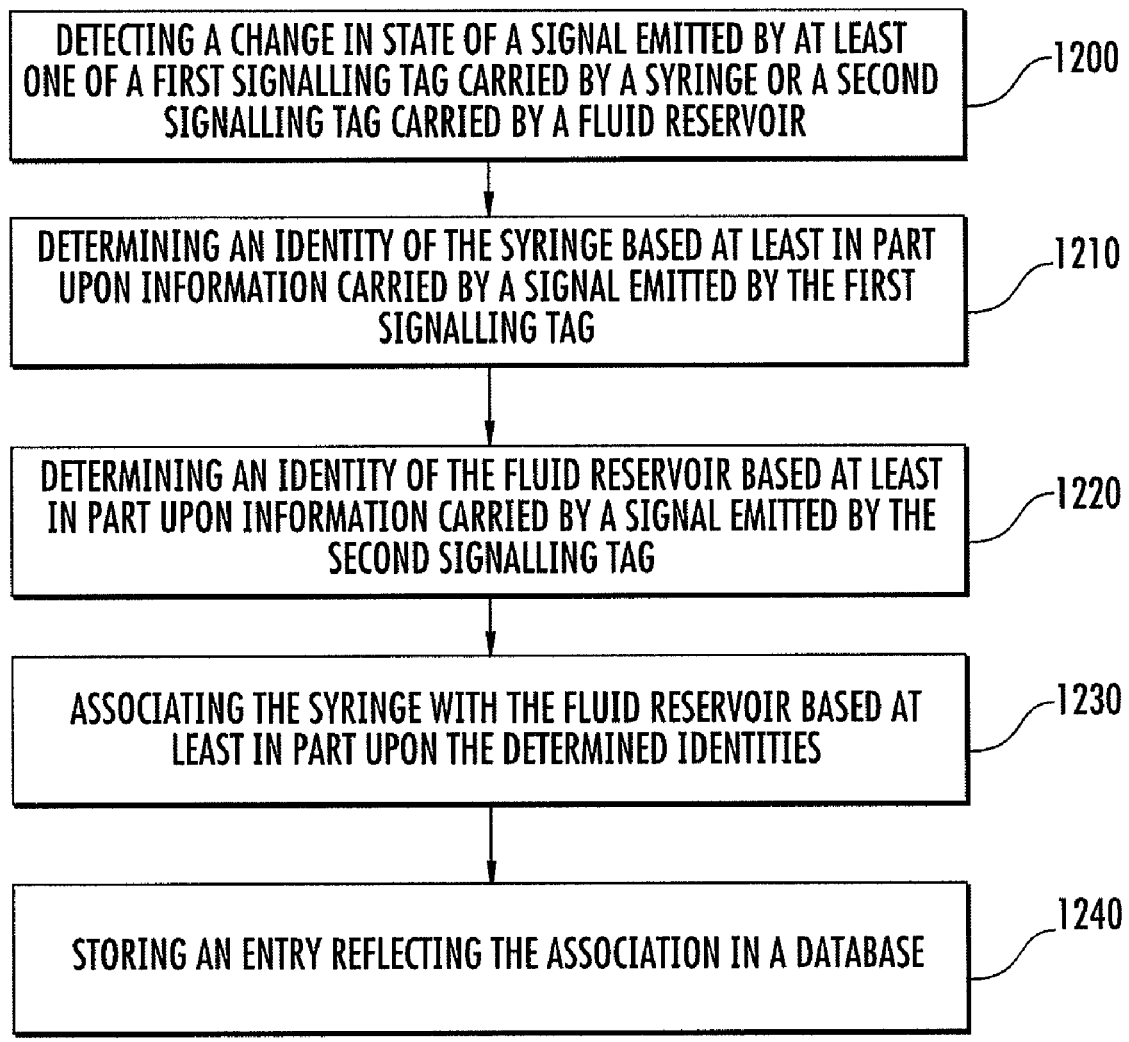

FIG. 11 illustrates a screenshot of a database illustrating a history of medications transferred to an IV bag according to an exemplary embodiment of the present invention, such as may have been generated following the steps of FIG. 10; and FIG. 12 is a flowchart according to an exemplary method for monitoring a transfer of fluid between a syringe and a fluid reservoir according to an exemplary embodiment of the present invention.

DETAILED DESCRIPTION

Some embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like reference numerals refer to like elements throughout.

Figure 1:
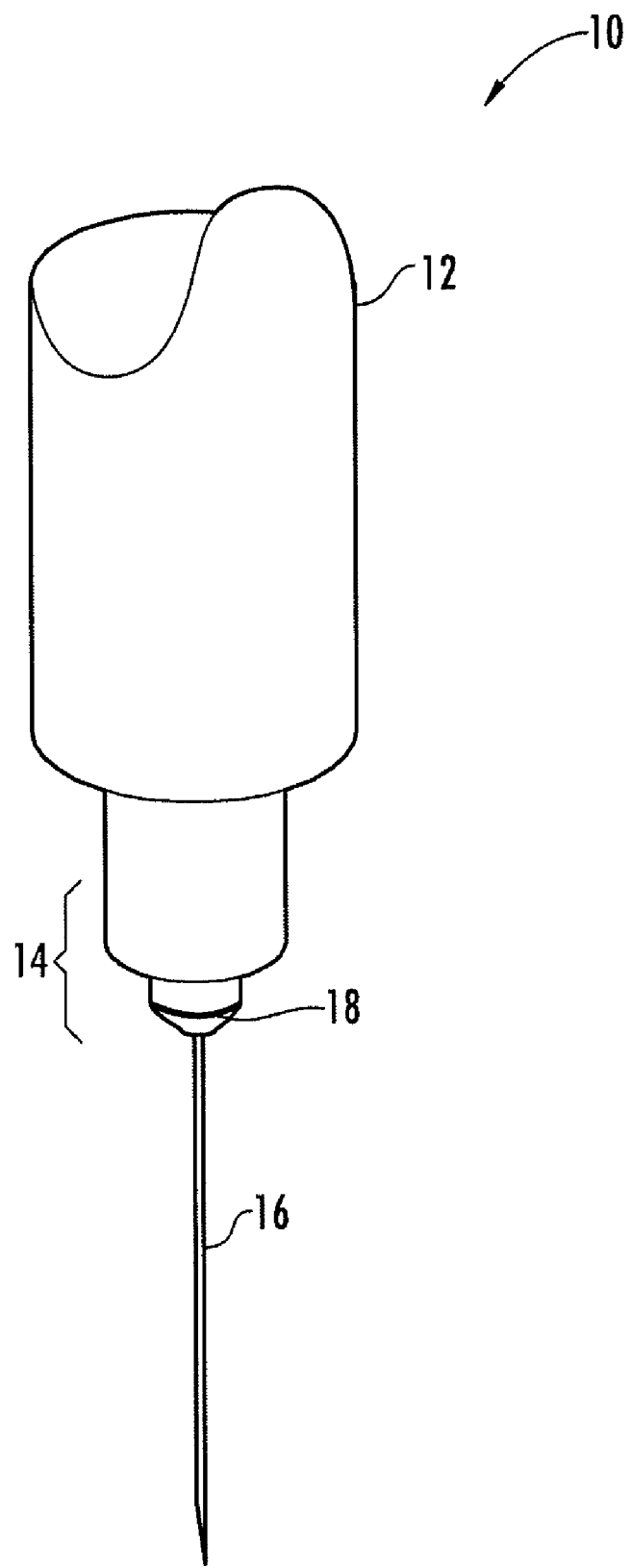
FIG. 1 illustrates a syringe according to an exemplary embodiment of the present invention.

FIG. 1 illustrates a syringe 10 according to an exemplary embodiment of the present invention. As used herein, "exemplary" merely means an example and as such represents one example embodiment for the invention and should not be construed to narrow the scope or spirit of the invention in any way. It will be appreciated that the scope of the invention encompasses many potential embodiments in addition to those illustrated and described herein for purposes of example. As such, while FIG. 1 illustrates one example of a configuration of a syringe, numerous other configurations may also be used to implement embodiments of the present invention.

The syringe 10 comprises a tubular chamber 12 for holding fluid to be transferred between the syringe and a fluid reservoir. In this regard, and as is well known in the art, a syringe comprises a plunger (not illustrated) that slides within the tubular chamber 12 and may be used to withdraw fluid from a fluid reservoir to transfer fluid from the fluid reservoir to the tubular chamber 12 and to transfer fluid from the tubular chamber 12 to a fluid reservoir. In this regard, a "fluid reservoir" may comprise any container, tube, pipe, chamber, or the like for holding, storing, conveying, transferring, and/or transporting (as well as similar functions) fluid and may comprise, for example, a medicine vial, IV bag, IV injection port, IV line, bottle or the like. Accordingly, the syringe 10 comprises an embodiment of a fluid reservoir, as the tubular chamber 12 provides for holding fluid. The syringe 10 further comprises a distal end 14, which provides a point of attachment for a needle 16 that enables the transfer of fluid between the syringe 10 and a fluid reservoir. In this regard, the needle 16 may be inserted through a membrane (e.g., a "septum") of a fluid reservoir to enable transfer of fluid between the syringe 10 and the fluid reservoir.

In at least some embodiments, a signaling tag 18 is carried by the syringe 10. In at least some embodiments, the signaling tag 18 comprises a radio frequency (RF) tag. Accordingly, the description herein of embodiments of the invention refers to the signaling tag 18 as an RF tag 18 for purposes of example to describe a radio frequency signal as one type of signal that may be emitted by a signaling tag. It will be appreciated, however, that the signaling tag 18 may be configured to emit detectable signals other than radio frequency, such as, for example, ultrasound signals, optical signals, and/or the like. Similarly, it will be appreciated that wherever RF tag is used herein, it is merely one example of a signaling tag and accordingly other types of signaling tags may be substituted for the RF tag.

In some embodiments, the RF tag 18 may be disposed proximate to and/or carried by the distal end 14 such that the RF tag 18 is molded into or otherwise affixed to the distal end 14. In at least some embodiments, the RF tag 18 is removeably attachable to the syringe 10 such that the RF tag 18 may be reused even when the syringe 10 comprises a single-use disposable syringe. In such embodiments, the RF tag 18 may be embodied on a clip, ring, or other structure carried by the distal end 14 due to friction between an inner surface of the structure containing the RF tag 18 and an outer surface of the syringe 10. The RF tag 18 and/or an adaptor configured to carry the RF tag 18 may comprise threading, such as a Luer lock-type fitting, to facilitate attachment to the syringe 10. Accordingly, the syringe 10 may comprise a corresponding threaded portion for receiving a threaded RF tag 18 and/or a threaded adaptor configured to carry an RF tag 18. Additionally or alternatively, a structure comprising the RF tag 18 may be placed on the syringe 10 and held in place by an adhesive. Further, in some embodiments, the syringe 10 may comprise a molded slot, tray, or other receptacle configured to receive an RF tag 18 that may be inserted in such a receptacle. It will be appreciated, however, that the RF tag 18 is not limited to being disposed proximate to the distal end 14 and may be carried elsewhere on the syringe, including, for example, on or within the tubular chamber 12 or on the plunger.

The RF tag 18 may be positioned such that when the needle 16 is inserted through a membrane of a fluid reservoir for transferring fluid between the syringe and the fluid reservoir, the RF tag 18 comes into a sufficient proximity with a second RF tag carried by the fluid reservoir to trigger a change in the state of a signal emitted by at least one of the RF tag 18 and the second RF tag. In some embodiments, "sufficient proximity" comprises the RF tag 18 and second RF tag being within a predefined distance of each other.

Figure 2:
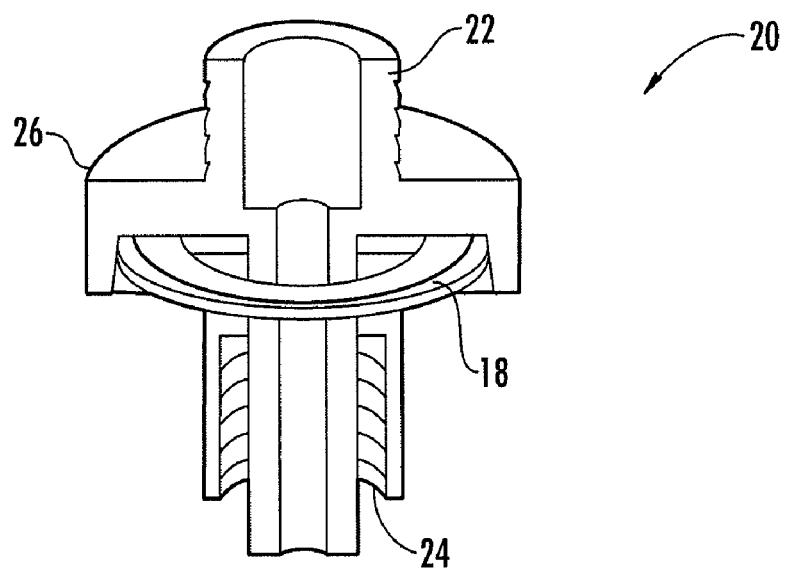
FIG. 2 illustrates a syringe adapter according to an exemplary embodiment of the present invention.

In some embodiments, a syringe 10 may be assembled, such as by a medical technician, from a plurality of components prior to use. In this regard, FIG. 2 illustrates a syringe adapter 20 according to an exemplary embodiment of the present invention. The syringe adapter 20 comprises a first Luer lock 22 at a proximal end of the syringe adapter 20 for attaching to the tubular chamber 12. The syringe adapter 20 further comprises a second Luer lock 24 at a distal end of the syringe adapter 20 for attaching to a needle 16. In addition, a syringe adapter 20 according to an exemplary embodiment comprises a molded adapter 26 housing the RF tag 18. Accordingly, in embodiments wherein a syringe 10 is assembled using a syringe adapter 20, the syringe adapter 20 comprises the distal end of the syringe providing the point of attachment for the needle 16 and may carry the RF tag 18.

Figure 3:
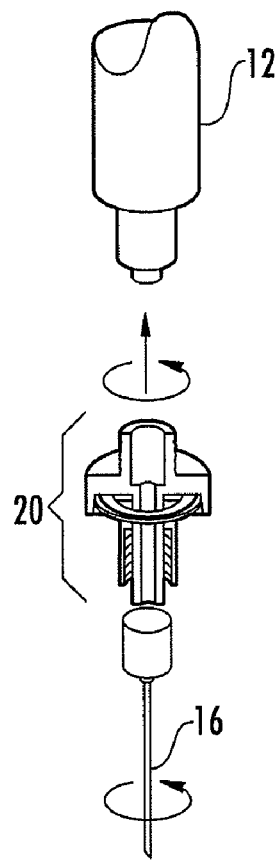
FIG. 3 illustrates a syringe according to an exemplary embodiment of the present invention.

FIG. 3 illustrates assembly of a syringe from components including a tubular chamber 12, syringe adapter 20, and needle 16.

Figure 4:
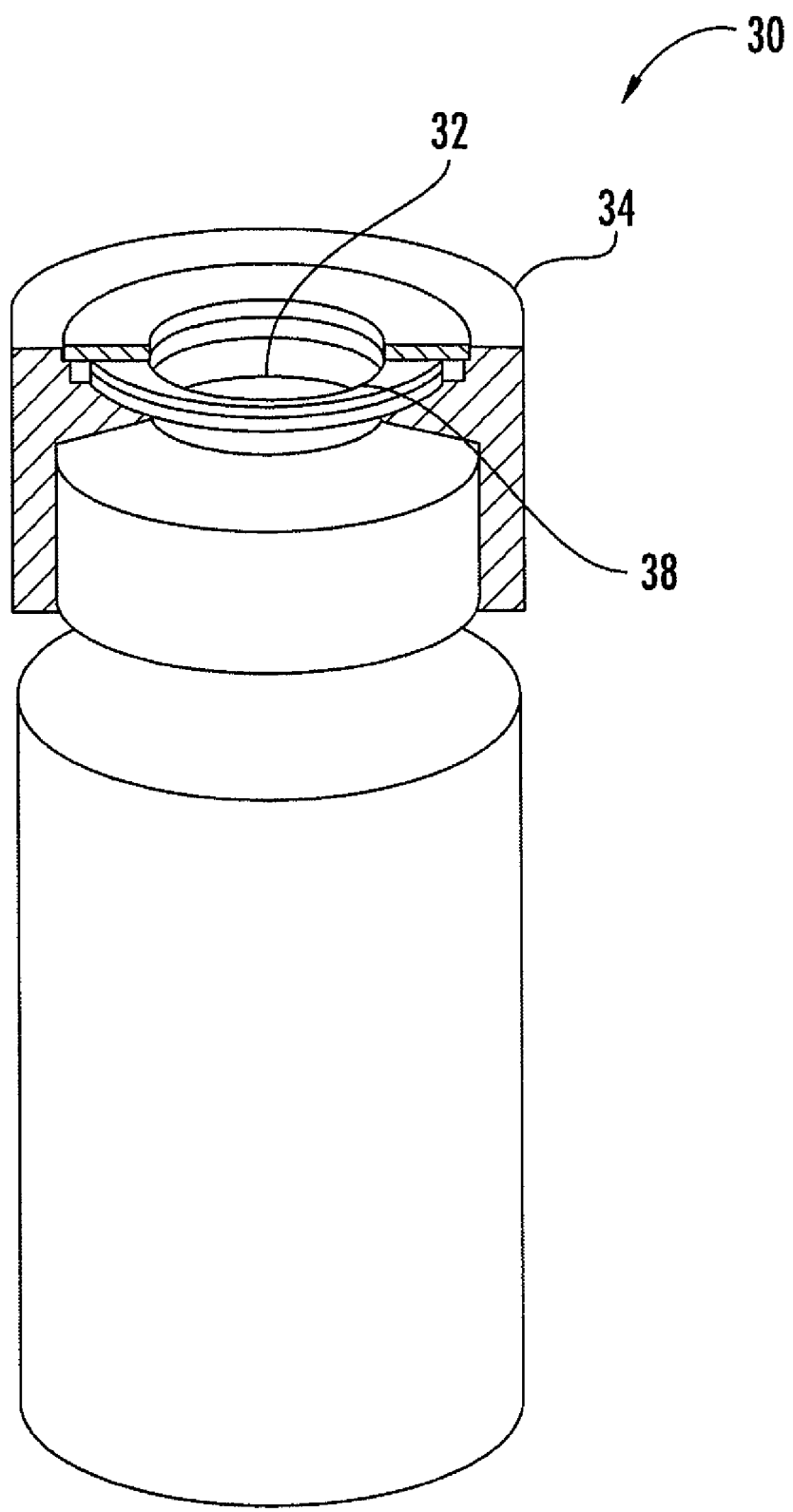
FIG. 4 illustrates a medicine vial according to an exemplary embodiment of the present invention.

FIG. 4 illustrates a medicine vial 30 according to an exemplary embodiment of the present invention. In this regard, a medicine vial comprises one type of fluid reservoir. The medicine vial 30 comprises a membrane 32 through which the needle 16 of a syringe 10 may be inserted to transfer fluid, such as a medication or drug, from the medicine vial 30 to the syringe 10. The medicine vial 10 further comprises a cap 34 holding an RF tag 38. The cap 34 may be attached to the medicine vial 10 by the manufacturer (e.g., crimped on the body of the medicine vial). Alternatively, the cap 34 may comprise a removable cap that may be placed on a medicine vial, such as by a technician, prior to transfer of fluid from the medicine vial. The cap 34 may be held on the medicine vial by any means, including, for example, friction, an adhesive, and/or the like. Accordingly, embodiments wherein the cap 34 is removable may facilitate use of the cap 34 on multiple medicine vials.

Figure 5:
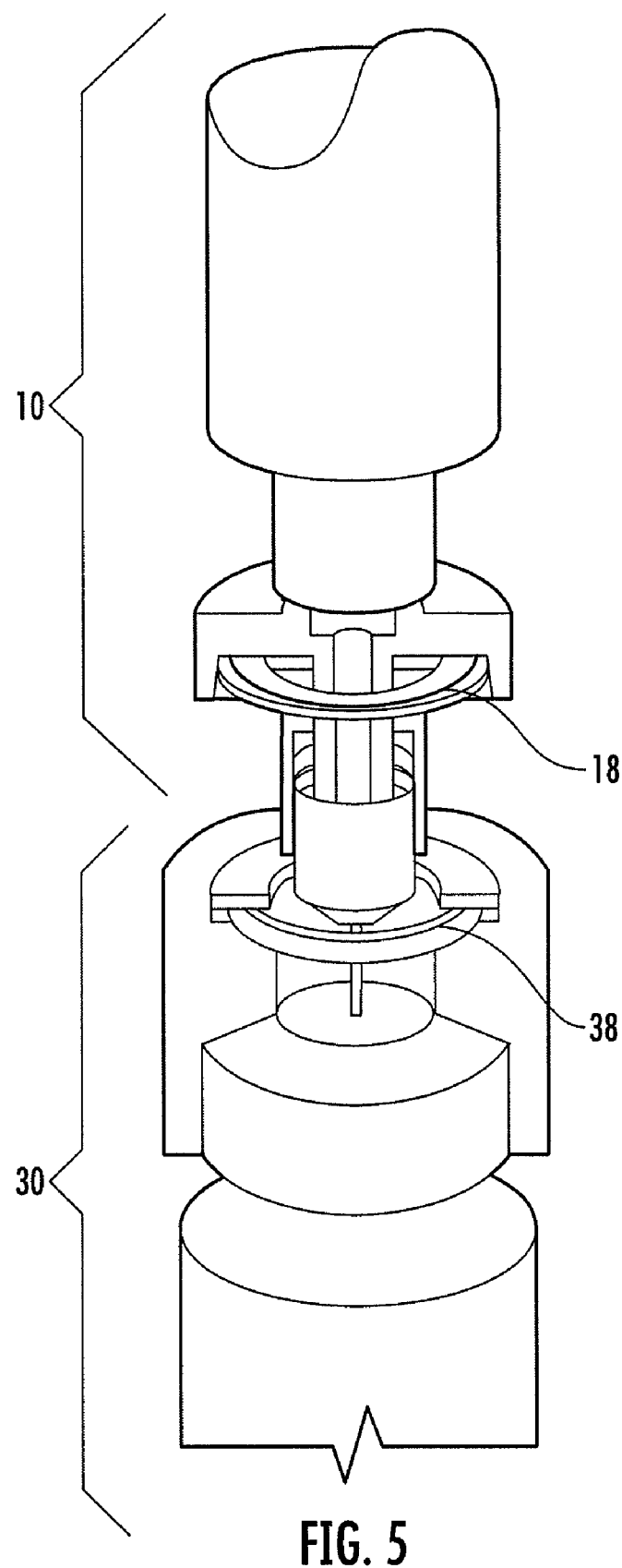
FIG. 5 illustrates a syringe according to an exemplary embodiment of the present invention inserted into a medicine vial according to an exemplary embodiment of the present invention.

FIG. 5 illustrates a syringe 10 according to an exemplary embodiment of the present invention inserted into a medicine vial 30 according to an exemplary embodiment of the present invention. Although the syringe 10 is illustrated in FIG. 5 directly inserted in the medicine vial 30, in some embodiments an intermediate conduit may be disposed between the medicine vial 30 and the syringe 10 during a fluid transfer. The intermediate conduit may serve to prevent fluid and/or vapors from escaping during a transfer of fluid between the medicine vial 30 and the syringe 10. In this regard, a first end of the fluid conduit may be attached to the distal end of the syringe 10, such as through a Luer lock fitting. A second end of the fluid conduit opposite of the first end may contact with the medicine vial 30. In this regard, the second end may fit over the medicine vial 30, snap onto the medicine vial 30, lock onto a receptacle or adaptor disposed on the medicine vial 30, and/or the like. The intermediate conduit may comprise an assembly including a needle 16 that is enclosed by the intermediate conduit to prevent the escape of fluid and/or vapors during a transfer of fluid. Alternatively, the intermediate conduit may be fitted over the needle 16 so as to enclose the needle 16 to prevent the escape of fluid and/or vapors during a transfer of fluid. Thus a syringe (e.g., syringe 10) as referred to herein may further comprise such an intermediate conduit and the RF tag 18 may be disposed proximate the second end of the intermediate conduit (e.g., distal end of the syringe 10).

As illustrated in FIG. 5, the RF tag 18 and the RF tag 38 carried by the medicine vial 30 are positioned substantially parallel and in a close proximity to each other when the needle 16 is inserted through the membrane 32 of the medicine vial 30. In exemplary embodiments, the proximity between the RF tags 18 and 38 is sufficient to trigger a change in state of a signal emitted by at least one of the RF tags 18 and 38. This signal state change is indicative of an associative relationship between the medicine vial 30 and the syringe 10, and in exemplary embodiments of the invention is indicative of a transfer of fluid from the medicine vial 30 to the syringe 10. Depending on the particular embodiment of the RF tags 18 and 38, the sufficient proximity required may, for example, comprise a predefined distance or predefined optimum range (e.g., greater than a minimum distance and less than a maximum distance). Accordingly, the RF tags may be positioned and/or one or more of the distal end of the syringe 10 and the cap 34 may be formed (e.g., molded, machined, and/or the like) to facilitate the RF tags 16 and 18 coming within the appropriate proximity of each other to trigger a signal state change in at least one of the tags when the needle 16 is inserted through the membrane 32.

It will be appreciated that the signal state change may comprise any change in state of the RF tag 18 and/or RF tag 38 triggered by the RF tags 18 and 38 coming within sufficient proximity of each other due to insertion of the needle 16 through the membrane 32. For example, when the needle 16 is not inserted through the membrane 32, an antenna of at least one of the RF tags 18 and 38 may be detuned such that the antenna does not emit a readable or otherwise detectable signal. When the RF tags 18 and 38 come within sufficient proximity of each other, the RF tags 18 and 38 may couple, causing the detuned antenna to become tuned and emit a readable signal. Accordingly, in some embodiments, the signal state change comprises emission of a readable signal from at least one of the RF tags 18 and 38 when the RF tag(s) was not previously emitting a readable signal.

In another example, when the needle 16 is not inserted through the membrane 32, an antenna of at least one of the RF tags 18 and 38 may be configured to emit a readable or otherwise detectable signal. When the RF tags 18 and 38 come within sufficient proximity of each other, the RF tags 18 and 38 may couple, causing the antenna to become detuned and cease to emit a readable signal. Accordingly, in some embodiments, the signal state change comprises cessation of emission of a readable signal from at least one of the RF tags 18 and 38 when the RF tag(s) was previously emitting a readable signal.

In yet another example, the RF tags 18 and 38 may each comprise a primary antenna and a secondary antenna. The primary antenna may be configured to emit a readable or otherwise detectable signal when the needle 16 is not inserted through the membrane 32. The secondary antenna may be configured to be detuned such that neither of secondary antennas emit a readable signal when the needle 16 is not inserted through the membrane 32. When the RF tags 18 and 38 come within sufficient proximity of each other, the secondary antennas may be activated and emit readable signals. Accordingly, in some embodiments, the signal state change comprises emission of a second or new readable signal from at least one of the RF tags 18 and 38. The new emitted signal may be in addition to that initially emitted by the primary antennas or in lieu of the initial signal emitted when the needle 16 was not inserted through the membrane 32.

In a further example, one or more of the RF tags 18 and 38 may be configured to emit a signal having a first communication field and/or a first frequency when the needle 16 is not inserted through the membrane 32. When the RF tags 18 and 38 come within sufficient proximity of each other when the needle 16 is inserted through the membrane 32, one or both of the RF tags 18 and 38 may be configured to emit a signal having a second communication field and/or a second frequency. A reader, antenna, and/or interrogator used to monitor a state of a signal emitted by the RF tag 18 and/or RF tag 38 may be configured to differentiate between the first and second communication fields and/or frequencies. In some embodiments, the first communication field or frequency may comprise a near-field UHF signal that is readable only from a relatively close proximity to the RF tags emitting a signal having the first communication field or frequency. The second communication field or frequency may comprise a far-field UHF signal that is readable from a farther distance away from the RF tags than the first signal. Accordingly, a reader and/or an antenna in communication with the reader may be positioned at a sufficient distance from an emitting RF tag such that only the signal having the second communication field or frequency is detectable such that the insertion of the needle 16 through the membrane 32 and by proxy the transfer of fluid may be detected.

In another example, one or more of the RF tag 18 and RF tag 38 may vary the amplitude (e.g., increasing the amplitude, decreasing the amplitude, or the like) of an emitted signal such that a reader may detect the amplitude variation when the RF tags 18 and 38 come within sufficient proximity of each other, thus indicating a transfer of fluid.

It will be appreciated that the above described example changes in signal state are merely examples of some embodiments of the invention. Accordingly, embodiments of the invention may utilize any measurable change in signal state triggered when the RF tag 18 and RF tag 38 come within sufficient proximity of each other.

Figure 6:
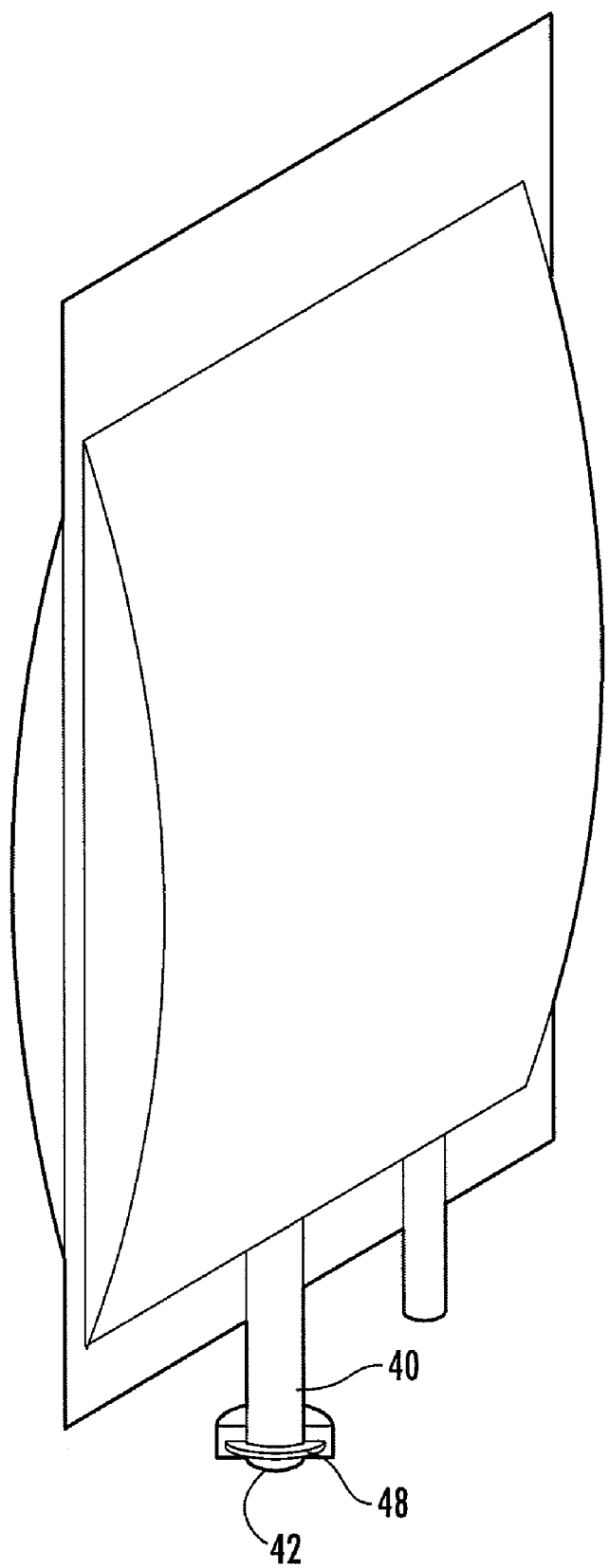
FIG. 6 illustrates an IV bag according to an exemplary embodiment of the present invention.
Figure 7:
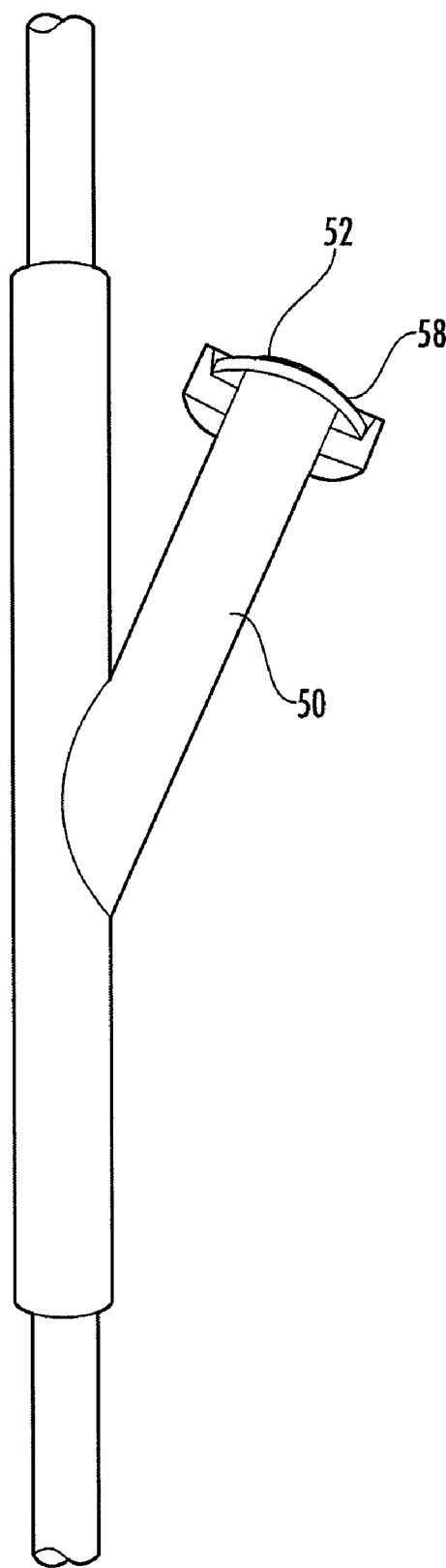
FIG. 7 illustrates an IV injection port according to an exemplary embodiment of the present invention.

Further, although the above-described signal state changes are described in the context of a RF tag 38 of a medicine vial 30, it will be appreciated that a state change can be monitored when the needle 16 is inserted through a membrane of any fluid reservoir carrying an RF tag that comes within sufficient proximity of the RF tag 18. In this regard, FIG. 6 illustrates an IV bag according to an exemplary embodiment of the present invention. The IV bag may comprise an injection port 40 including a membrane 42 at the end of the injection port through which the needle 16 of a syringe may be inserted. The injection port 40 may further carry an RF tag 48 that may be positioned such that when the needle 16 of a syringe 10 is inserted through the membrane 42, the RF tag 18 comes within sufficient proximity of the RF tag 48 to trigger a state change in at least one of the RF tag 18 and 48. This signal state change is indicative of an associative relationship between the syringe 10 and the IV bag, and in an exemplary embodiment is indicative of a transfer of fluid from the syringe 10 to the IV bag. The signal state change may comprise any of the signal state changes described above in connection with the RF tag 38 of a medicine vial 10. Similarly, FIG. 7 illustrates an IV injection port, such as may be used to transfer fluid directly into an IV line, according to an exemplary embodiment of the present invention. The IV injection port may comprise an injection port 50 including a membrane 52 at the end of the injection port through which the needle 16 of a syringe 10 may be inserted. The injection port 50 may further carry an RF tag 58 that may be positioned such that when the needle 16 of a syringe 10 is inserted through the membrane 52, the RF tag 18 comes within sufficient proximity of the RF tag 58 to trigger a state change in at least one of the RF tag 18 and 58. This signal state change is indicative of an associative relationship between the syringe 10 and the IV injection port, and in an exemplary embodiment is indicative of a transfer of fluid from the syringe 10 to the IV injection port (e.g., into an IV line). The signal state change may comprise any of the signal state changes described above in connection with the RF tag 38 of a medicine vial 10.

It will further be appreciated that embodiments of the invention may provide for detecting an associative relationship between any two fluid reservoirs and not just between a syringe and a second fluid reservoir. In this regard, a first fluid reservoir may carry a first RF tag and a second fluid reservoir may carry a second RF tag. The first and second RF tags may be positioned such that when a fluid transfer point of the first fluid reservoir comes into contact with a fluid transfer point of the second fluid reservoir (e.g., such that the fluid transfer points are coupled to enable transfer of fluid between the first and second fluid reservoirs) and thus by way the first and second RF tags come within a sufficient proximity of each other, a change in state of a signal emitted by at least one of the first and second RF tags is triggered. The signal state change is indicative of an associative relationship between the first and second fluid reservoirs. In some embodiments, the associative relationship is indicative of a transfer of fluid between the first and second fluid reservoirs. The signal state change triggered when the first and second RF tags come within a sufficient proximity of each other may comprise any of the example signal state changes discussed above with respect to a RF tag 18 of a syringe 10 and a RF tag 38 of a medicine vial 30. The first and second fluid reservoirs may comprise, for example, portions of an IV line and/or IV line connectors that may be fitted together. In one embodiment, the first fluid reservoir may comprise an IV bag, such as that illustrated in FIG. 6, and the second fluid reservoir may comprise an IV line that may be connected to the IV bag by the respective fluid transfer points of the IV line and IV bag. Thus, where a syringe 10 is described in connection with a fluid transfer between a syringe 10 and a fluid reservoir, it will be appreciated that the syringe 10 is merely cited as an example of one type of fluid reservoir. Further, where the puncturing of a septum with the needle 16 is described, it will be appreciated that a first and second fluid reservoir may engage each other (e.g., for the transfer of fluids) such that they come within sufficient proximity to trigger a change in state of a signal emitted by a first RF tag carried by the first fluid reservoir and/or of a signal emitted by a second RF tag carried by the second fluid reservoir for the transfer of fluids in other ways. For example, a first and second fluid reservoir may engage each other through the coupling of the fluid transfer point (e.g., a connector) of the first fluid reservoir with the fluid transfer point (e.g., a connector) of the second fluid reservoir.

It will be further appreciated that RF tags described herein may be either active RF tags or passive RF tags. Accordingly, a reader used to monitor a state of a signal emitted by an RF tag may be configured to passively monitor the signal state or to actively interrogate the RF tag. Accordingly, any signal emitted by an RF tag may be emitted in response to being interrogated by a reader, if the tag is embodied as a passive tag.

Figure 8:
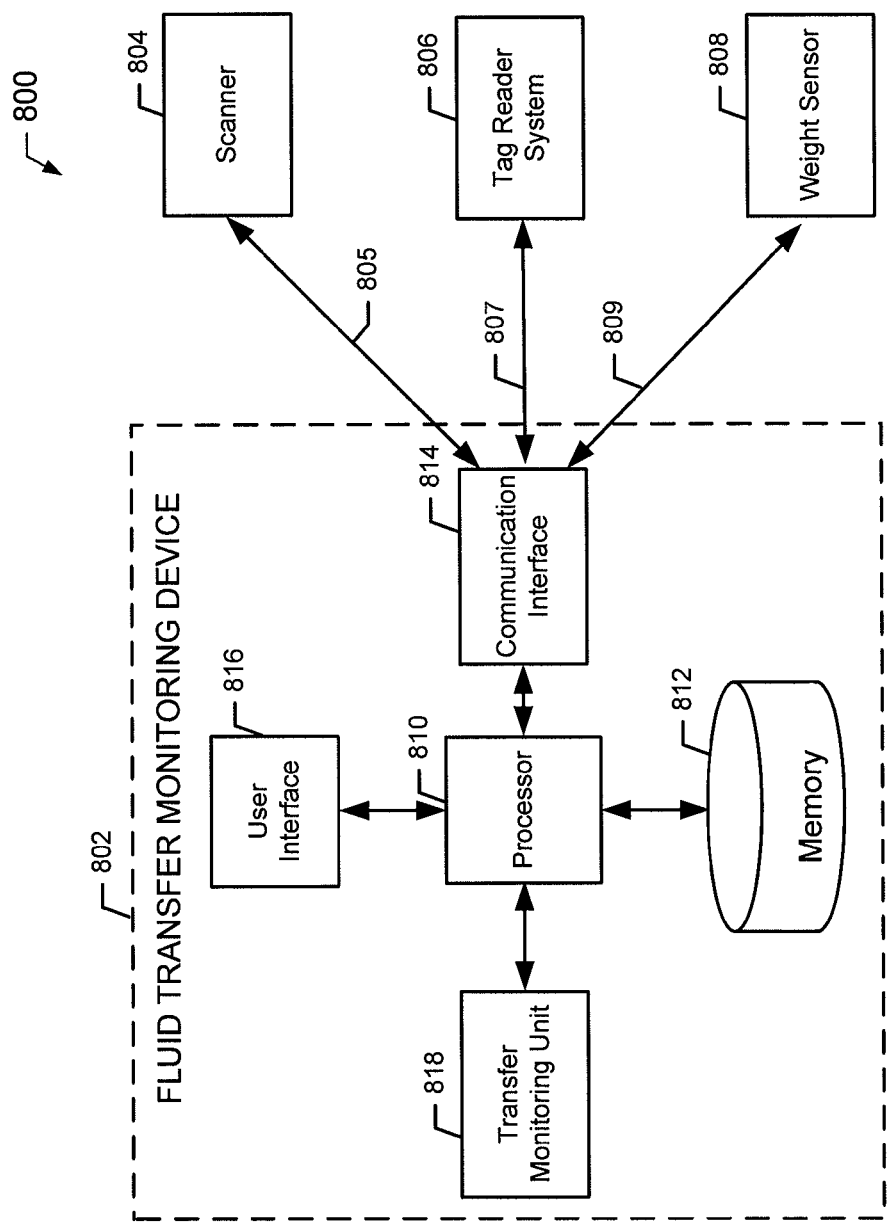
FIG. 8 illustrates a block diagram of a system for monitoring a transfer of fluid between a syringe and a fluid reservoir according to an exemplary embodiment of the present invention.

Embodiments of the invention further provide systems and devices for monitoring a transfer of fluid between a syringe 10 and a fluid reservoir through detection of a change in state of a signal emitted by the RF tag 18 and/or an RF tag carried by the fluid reservoir. In this regard, FIG. 8 illustrates a block diagram of a system 800 for monitoring a transfer of fluid between a syringe and a fluid reservoir according to an exemplary embodiment of the present invention. The system 800 comprises a fluid transfer monitoring device 802, scanner 804, tag reader system 806, and weight sensor 808. The fluid transfer monitoring device 802 may be in communication with the scanner 804 over the communications link 805. The fluid transfer monitoring device 802 may further be in communication with the tag reader system 806 over the communications link 807. The fluid transfer monitoring device 802 may additionally be in communication with the weight sensor 808 over the communications link 809. The fluid transfer monitoring device 802 may be embodied as or on any computing device or plurality of computing devices.

The scanner 804 may be embodied as any device configured to read and identify a barcode, human readable text and/or other distinguishing feature, such as may be located on an object, such as, for example, a syringe, medicine vial, IV bag, and/or the like for purposes of identifying the object. The tag reader system 806 may be embodied as a signaling tag (e.g., an RF tag) reader/antenna configured to read a signal emitted by the RF tag 18 and/or an RF tag carried by a fluid reservoir such that a change in state of the signal may be detected. The tag reader system 806 may further be configured to read a signal emitted by an RF tag to identify the object (e.g., syringe, medicine vial, IV bag, or other fluid reservoir) carrying the RF tag. Depending on embodiments of the RF tag, the tag reader system 806 may passively read an emitted signal (e.g., for an active RF tag) or to actively interrogate an RF tag (e.g., for a passive RF tag).

The tag reader system 806 may be located anywhere within sufficient proximity of a location where fluid is transferred between a syringe 10 and a fluid reservoir to first detect the identity of the object (e.g., syringe, medicine vial, IV bag, or other fluid reservoir) and secondly detect a change in state of the RF tag or tags. The tag reader system 806 may be mounted, for example, within a laminar hood. The system 800 may comprise a plurality of tag readers and/or antennas 806 mounted in various location at which fluid transfers occur and/or locations at which objects may be identified so as to lookup a fluid transfer history associated with the object, such as may be stored in a database by the fluid transfer monitoring device 802 according to exemplary embodiments of the present invention. The weight sensor 808 may comprise any scale or other means configured to weigh a fluid reservoir so that a volume of fluid contained in the fluid reservoir may be calculated.

The weight sensor 808 may further comprise an scanner 804 and/or tag reader system 806 positioned on the weight sensor 808 such that an identity of a fluid reservoir being weighed on the weight sensor 808 may be ascertained.

In some embodiments, the communications links 805, 807, and/or 809 comprise a direct wireline or wireless communications links. In other embodiments, the communications links 805, 807, and/or 809 comprise one or more networks (e.g., a local area network) through which devices of the system 800 are interfaced.

Referring now to the fluid transfer monitoring device 802, in an exemplary embodiment, the fluid transfer monitoring device 802 includes various means, such as a processor 810, memory 812, communication interface 814, user interface 816, and transfer monitoring unit 818 for performing the various functions herein described. These means of the fluid transfer monitoring device 802 as described herein may be embodied as, for example, hardware elements (e.g., a suitably programmed processor, combinational logic circuit, and/or the like), a computer program product comprising computer-readable program instructions (e.g., software or firmware) stored on a computer-readable medium (e.g. memory 812) that is executable by a suitably configured processing device (e.g., the processor 810), or some combination thereof. The processor 810 may be embodied in a number of different ways. For example, the processor 810 may be embodied as a processing element, a coprocessor, a controller or various other processing means or devices including integrated circuits such as, for example, an ASIC (application specific integrated circuit) or FPGA (field-programmable gate array) or combinations thereof. In an exemplary embodiment, the processor 810 may be configured to execute instructions stored in the memory 812 or otherwise accessible to the processor 810. As such, whether configured by hardware or software methods, or by a combination thereof, the processor 810 may represent an entity capable of performing operations according to embodiments of the present invention while configured accordingly. Thus, for example, when the processor 810 is embodied as an ASIC, FPGA or the like, the processor 810 may comprise specifically configured hardware for conducting the operations described herein. Alternatively, as another example, when the processor 810 is embodied as an executor of program instructions, the instructions may specifically configure the processor 810 to perform the algorithms and operations described herein. However, in some cases, the processor 810 may be a processor of a specific device adapted for employing embodiments of the present invention by further configuration of the processor 810 by instructions for performing the algorithms and operations described herein. Although illustrated in FIG. 8 as a single processor, in some embodiments the processor 810 comprises a plurality of processors. The plurality of processors may be embodied on a single computing device or distributed across a plurality of computing devices.

The memory 812 may include, for example, volatile and/or non-volatile memory. The memory 812 may be configured to store information, data, applications, instructions, or the like for enabling the fluid transfer monitoring device 802 to carry out various functions in accordance with exemplary embodiments of the present invention. For example, in at least some embodiments, the memory 812 is configured to buffer input data for processing by the processor 810. Additionally or alternatively, in at least some embodiments, the memory 812 is configured to store program instructions for execution by the processor 810. The memory 812 may comprise one or more databases that store information in the form of static and/or dynamic information. This stored information may be stored and/or used by the transfer monitoring unit 818 during the course of performing its functionalities.

The communication interface 814 may be embodied as any device or means embodied in hardware, a computer program product comprising computer readable program instructions (e.g., software and/or firmware) stored on a computer readable medium (e.g., the memory 812) and executed by a processing device (e.g., the processor 810), or a combination thereof that is configured to receive and/or transmit data from/to a remote device, such as a scanner 804, tag reader system 806, and/or weight sensor 808 over the communications links 805, 807, and 809, respectively. In at least one embodiment, the communication interface 814 is at least partially embodied as or otherwise controlled by the processor 810. The communication interface 814 may include, for example, an antenna, a transmitter, a receiver, a transceiver and/or supporting hardware or software for enabling communications with devices of the system 800. The communication interface 814 may be configured to receive and/or transmit data using any protocol that may be used for communications with devices of the system 800. In at least some embodiments, the communication interface 814 is configured to receive an indication of a scanned identification code, such as a barcode from the scanner 804. In an exemplary embodiment, the communication interface 814 is additionally or alternatively configured to receive an indication of a detected state of a signal emitted by an RF tag from the tag reader system 806. The communications interface 814 is configured in at least some embodiments to receive an indication of a weight of an object, such as a fluid reservoir from the weight sensor 808. The communication interface 814 may additionally be in communication with the memory 812, user interface 816, and/or transfer monitoring unit 818, such as via a bus.

The user interface 816 may be in communication with the processor 810 to receive an indication of a user input and/or to provide an audible, visual, mechanical, or other output to the user. As such, the user interface 816 may include, for example, a keyboard, a mouse, a joystick, a display, a touch screen display, a microphone, a speaker, and/or other input/output mechanisms. The user interface 816 may accordingly provide means to provide historical information about fluid transfers and/or information about a history of fluids introduced into a fluid reservoir through fluid transfers to a user, such as by displaying information on a display. The user interface 816 may be in communication with the memory 812, communication interface 814, and/or transfer monitoring unit 818, such as via a bus.

The transfer monitoring unit 818 may be embodied as various means, such as hardware, a computer program product comprising computer readable program instructions (e.g., software and/or firmware) stored on a computer readable medium (e.g., the memory 812) and executed by a processing device (e.g., the processor 810), or some combination thereof and, in one embodiment, is embodied as or otherwise controlled by the processor 810. In embodiments where the transfer monitoring unit 818 is embodied separately from the processor 810, the transfer monitoring unit 818 may be in communication with the processor 810.

In at least some embodiments, the transfer monitoring unit 818 is configured to identify a fluid reservoir (e.g., a syringe, medicine vial, IV bag, and/or other fluid reservoir) based at least in part upon information carried by a signal emitted by an RF tag carried by the object. In this regard, an RF tag may emit a unique signature or signal detectable by the tag reader system 806 which is associated with the fluid reservoir. The association may be stored in a database, such as may be stored in the memory 812. Accordingly, the transfer monitoring unit 818 may be configured to receive identification information carried by a signal detected by the tag reader system 806 and emitted by an RF tag and look up the identification information in the database to determine the identity of the associated fluid reservoir.

The association between an RF tag and a fluid reservoir may be determined by a manufacturer of the object, such as when the manufacturer distributes objects with RF tags embodied thereon. This association may then be entered into the database, for example, when the fluid reservoir is received into a facility's inventory. Additionally or alternatively, the transfer monitoring unit 818 may be configured to generate an association. For example, a medical technician may place an RF tag on a fluid reservoir. The fluid reservoir may comprise a barcode or other identification information uniquely identifying the fluid reservoir. If this identification information may be optically scanned, such as in the case of a barcode, a medical technician may scan the identification information with the scanner 804. The transfer monitoring unit 818 may receive the identification information and generate an entry in the database for the fluid reservoir. The technician may then place the fluid reservoir and RF tag carried thereby within range of the tag reader system 806 so that the tag reader system 806 may read a signal emitted by the RF tag. In some embodiments, the emitted signal including identification information used to uniquely identify the fluid reservoir may comprise a signal emitted when the RF tag comes within sufficient proximity of another RF tag. Accordingly, the tag reader system 806 may further comprise, for example, a detuned RF tag that may trigger an appropriate change in state in the RF tag carried by the fluid reservoir when brought in sufficient proximity so that the tag reader system 806 may read the identifying signal. The transfer monitoring unit 818 may then associate information carried by the emitted signal with the identification information such that the fluid reservoir may be uniquely identified by a signal emitted by an RF tag carried thereby.

The transfer monitoring unit 818 is configured in at least some embodiments to monitor the state of a signal emitted by an RF tag, which is read by the tag reader system 806. The transfer monitoring unit 818 may be further configured to detect a change in state of the signal triggered by an RF tag 18 carried by a syringe 10 coming within a sufficient proximity of an RF tag carried by a fluid reservoir (e.g., an RF tag 38 carried by a medicine vial 10, an RF tag 48 carried by an IV bag, and/or the like) when the needle 16 pierces a membrane of the fluid reservoir. This signal state change may be indicative of a transfer of fluid between a syringe 10 and the fluid reservoir. When the transfer monitoring unit 118 detects the change in state, the transfer monitoring unit 118 may be configured to determine an identity of the syringe and of the fluid reservoir involved in the transfer through identifying information carried by signals emitted by the respective RF tags. The transfer monitoring unit 818 may then associate the syringe 10 with the fluid reservoir so as to indicate that fluid was transferred between the syringe 10 and the fluid reservoir. The transfer monitoring unit 818 may further store an entry reflecting the association in a database so as to build a history of the transfer of fluid. The entry may further comprise a time stamp noting a time and date at which the transfer took place.

Similarly, the transfer monitoring unit 118 is configured in at least some embodiments to monitor the state of a first RF tag carried by a first fluid reservoir and/or of a second RF tag carried by a second fluid reservoir. The transfer monitoring unit 818 may be further configured to detect a change in state of the signal(s) triggered by the first RF tag coming within a sufficient proximity of the second RF tag when a fluid transfer point of the first fluid reservoir comes into contact with a fluid transfer point of the second fluid reservoir (e.g., such that the first fluid transfer point and second fluid transfer point are coupled to enable a transfer of fluid between the first and second fluid reservoirs). This signal state change may be indicative of a transfer of fluid between the first and second fluid reservoirs. When the transfer monitoring unit 118 detects the change in state, the transfer monitoring unit 118 may be configured to determine an identity of the first fluid reservoir and of the second fluid reservoir involved in the transfer through identifying information carried by signals emitted by the respective RF tags. The transfer monitoring unit 818 may then associate the first fluid reservoir with the second fluid reservoir so as to indicate that fluid was transferred between the first fluid reservoir and the second fluid reservoir. The transfer monitoring unit 818 may further store an entry reflecting the association in a database so as to build a history of the transfer of fluid. The entry may further comprise a time stamp noting a time and date at which the transfer took place. In this regard, the transfer monitoring unit 118 is configured in at least some embodiments to detect a change in state indicating an associative relationship and/or transfer of fluids between two fluid reservoirs, wherein neither of the two fluid reservoirs comprises a syringe 10.

The transfer monitoring unit 818 may be further configured to build a history of medication transferred to and/or from a fluid reservoir by storing a series of entries in the database. For example, the transfer monitoring unit 818 may detect fluid transfer between a medicine vial 30 and syringe 10. The fluid withdrawn from the medicine vial 30 into the syringe 10 may then be injected into an IV bag. Accordingly, the transfer monitoring unit 818 may detect a change in state of a signal emitted by the RF tag 18 and/or RF tag 48 when the needle 16 of the syringe 10 is inserted through the membrane 42 of the IV bag to inject the fluid into the IV bag. The transfer monitoring unit 818 may accordingly determine an identity of the syringe 10 and of the IV bag, associate the syringe 10 and the IV bag based at least in part upon the determined identities and store an entry reflecting the association in the database. Accordingly, the database may show entries for the particular IV bag reflecting that fluid was injected into the bag by the identified syringe that was transferred from a particular medicine vial. If, for example, multiple types of fluids (e.g., medications) are injected into an IV bag, the transfer monitoring unit 818 may further be configured to store entries reflecting a transfer history of each medication and may further store a timestamp associated with each entry so as to establish a timeline of fluid transfers associated with the IV bag.

Each fluid transfer entry stored by the transfer monitoring unit 818 may further indicate a volume of fluid transferred (e.g., a volume of fluid transferred from a medicine vial 10, a volume of fluid transferred to an IV bag, and/or the like). For example, a medical technician may weigh a medicine vial 30 using the weight sensor 808 before and after transferring fluid from the medicine vial 30 to a syringe 10. The transfer monitoring unit 818 may be configured to calculate the difference in weight before and after the fluid transfer and then calculate a volume of fluid transferred from the medicine vial 30 to the syringe 10 using a predefined density of the fluid contained in the medicine vial 30. This density may, for example, be stored in a database accessible to the transfer monitoring unit 818 and associated with the identity of the particular medicine vial 30. Similarly, a volume of fluid transferred to an IV bag from a syringe 10 may be calculated using before and after weights and known density of the fluid added to the IV bag and/or fluid already in the IV bag.

Referring now to FIG. 9, FIG. 9 illustrates a step-by-step process for monitoring a transfer of fluid from a medicine vial to a syringe according to an exemplary embodiment of the present invention using elements of the system 800. Operation 900 comprises a medical technician selecting a particular medicine vial 30. If the medicine vial 30 includes an integrated cap 34 and/or if the cap 34 is already carried by the medicine vial 30, the medical technician may remove a protective top lid. If a cap 34 is not already on the medicine vial 30, the medical technician may snap a cap 34 onto the medicine vial 30. The medical technician may further sanitize the top surface of the medicine vial 30, including the membrane 32, such as by using an alcohol swab. If necessary, the technician may associate the RF tag 38 carried by the cap 34 with the medicine vial, such as by scanning a barcode identifying the medicine vial using the scanner 804 and then reading a signal emitted by the RF tag 38 using the tag reader system 806, as previously described.

Operation 905 comprises the medical technician placing the medicine vial 30 on the weight sensor 808. The medicine vial may then be rotated (e.g., automatically and/or with physician assistance) such that the scanner 804 may determine the identity of the medicine vial 30. The tag reader system 806 may read a signal emitted by the RF tag 38 and the transfer monitoring unit 818 may associate the medicine vial identity determined by the scanner 804 with RF tag information determined by the tag reader system 806 Depending on the configuration of the RF tag 38, the weight sensor 808 may comprise a calibration RF tag that may couple with the RF tag 38 to trigger the RF tag 38 to emit an appropriate readable signal. The weight sensor 808 may then determine a weight of the medicine vial 30 prior to transferring fluid from the medicine vial 30 to a syringe 10. The transfer monitoring unit 818 may update the database entry for the medicine vial 30 to reflect the current weight of the medicine vial 30 and include a time stamp noting the time of weighing.

Operation 910 may comprise the medical technician assembling a syringe 10 (if necessary) using a syringe adapter 20. Operation 915 comprises the technician inserting the needle 16 through the membrane 32 of the medicine vial 10. The RF tag 18 may then come within sufficient proximity of the RF tag 38 to trigger a change in state of a signal emitted by at least one of the RF tags that is detected by the tag reader system 806. In some embodiments, the transfer monitoring unit 818 may be configured to provide the user with an indication when the RF tags are within sufficient proximity of each other, such as by illuminating a light, sounding an audible indicator, or providing a graphic indication through the user interface 816. The transfer monitoring unit 818 may then determine an identification of the particular syringe 10 and medicine vial 30 and generate an association there between to indicate that fluid was transferred from the medicine vial 30 to the syringe 10. The transfer monitoring unit 818 may then update the database with an entry reflecting the association. The technician may then withdraw the syringe 10 from the medicine vial 30 and place the medicine vial 30 on the weight sensor 808.

Operation 920 then comprises the tag reader system 806 reading a signal emitted by the RF tag 38 and the transfer monitoring unit 818 identifying the medicine vial 30 based at least in part upon information carried by the emitted signal. Depending on the configuration of the RF tag 38, the weight sensor 808 may, as before, comprise a calibration RF tag that may couple with the RF tag 38 to trigger the RF tag 38 to emit an appropriate readable signal. The weight sensor 808 may then determine a weight of the medicine vial 30 representative of the weight following transfer of fluid from the medicine vial 30 to a syringe 10. The transfer monitoring unit 818 may update the database entry for the medicine vial 30 to reflect the current weight of the medicine vial 30 and include a time stamp noting the time of weighing. The transfer monitoring unit 818 may further calculate a volume of fluid transferred from the medicine vial 30 and/or a volume of fluid remaining in the medicine vial 30 based at least in part upon a difference between the preliminary weight and the final weight and upon a predefined density of the fluid contained in the medicine vial 30. The transfer monitoring unit 818 may store the calculated volumes in the database.

Step 925 may optionally comprise the technician removing the needle 16 from the syringe 10, such as in embodiments wherein the syringe 10 was assembled using a syringe adapter 20. The technician may further place a cap on the distal end of the syringe 10 for sanitation purposes. The technician may then provide the filled syringe 10 and/or medicine vial 30 to a pharmacist located outside of the sterile environment for examination before the contents of the syringe 10 are administered to a patient. Operation 930 may then comprise the tag reader system 806 reading a signal emitted by the RF tag 18 of the syringe 10 so that the transfer monitoring unit 818 may identify the syringe 10. Depending on the configuration of the RF tag 18, the tag reader system 806 may comprise a calibration RF tag that may couple with the RF tag 18 to trigger the RF tag 18 to emit an appropriate readable signal. The transfer monitoring unit 818 may then retrieve database entries related to the identified syringe 10 and display on a display associated with the user interface 816 information about the transfer history of the fluid in the identified syringe 10 including, for example, the volume of fluid transferred, the identity of the medicine vial 10 from which the fluid was transferred, a time of the transfer, and/or the like.

FIG. 10 illustrates a step-by-step process for monitoring a transfer of a plurality of medications to an IV bag according to an exemplary embodiment of the present invention. In this regard, operation 1000 comprises weighing and generating a database entry for a medicine vial containing "Drug 'A'" similarly to operation 905 described above. Operation 1000 may further comprise weighing and generating a database entry representing an initial baseline weight and/or volume of an IV bag into which a volume of the Drug 'A' is to be injected. Operation 1005 comprises associating a particular syringe with the medicine vial containing Drug "A", and transferring a volume of Drug "A" to the syringe similarly to Operation 915 described above. Operation 1010 comprises weighing the medicine vial and generating a database entry for the medicine vial following transfer of fluid to the syringe. Operation 1015 comprises associating the syringe containing the transferred volume of Drug "A" with a particular IV bag. This association may be generated by the transfer monitoring unit 818, which may identify the syringe and the IV bag when the RF tag 18 carried by the syringe comes within sufficient proximity of the RF tag 48 carried by the IV bag when the needle of the syringe is inserted into the membrane of the injection port of the IV bag. The transfer monitoring unit 818 may further update the database with an entry reflecting this association. Operation 1020 comprises weighing the IV bag following transfer of Drug "A" from the syringe to the IV bag and the transfer monitoring unit 818 generating a database entry reflecting the transfer of a volume of Drug "A" to the IV bag. As a real-time measurement may be used to weigh the IV bag and/or the medicine vial containing Drug "A," the transfer monitoring unit 118 may be configured to determine whether any quantity of Drug "A" was wasted, such as due to spillage during the transfer. For example, based on an initial order, the injection weight of what Drug A should be may be known to be "X1." If the IV bag is pre-weighed and the weight is "W1" and after injection the total weight is less than "W1+X1," then the preparation may not be correct. Accordingly, the transfer monitoring unit 118 may be configured to notify a technician, such as through an audible or visual output to the user interface 816, that there is an insufficient amount of Drug A in the mixture.

Operation 1025 may comprise transferring an additional amount of Drug "A" from the medicine vial to the same syringe as used previously (e.g., if a greater volume of Drug "A" is to be added to the IV bag than the tubular chamber of the syringe is capable of holding). Again, the transfer monitoring unit 818 may identify the syringe and medicine vial, generate an association there between, and store a database entry reflecting the transfer in response to a change in state of a signal emitted by the RF tag 18 and/or RF tag 38. As indicated in FIG. 10, in this example, the type of medication (Drug "A") has remained the same for two transfers, but the RF tag ID has changed between the first vial and the second vial. This may occur, for example, a greater volume of the medication is needed than is remaining or otherwise contained in a single vial. The respective RF tags on the medicine vials may be supplied by the drug manufacturer and may, for example, include information indicating manufacturer name, drug name, expiration date, lot number, and/or the like. Operation 1030 comprises weighing the medicine vial containing Drug "A" following the second transfer and updating the database to reflect the additional volume of Drug "A" to the syringe. Operation 1035 then comprises again associating the syringe containing the transferred volume of Drug "A" with the IV bag when a signal state change is detected in a signal emitted by at least one of the RF tag 18 or RF tag 48 when the syringe is inserted into the injection port of the IV bag.

Operation 1040 comprises weighing and generating a database entry for a medicine vial containing "Drug 'B'" similarly to operation 905 described above. Operation 1040 may further comprise weighing and generating a database entry representing an initial baseline weight and/or volume of an IV bag into which a volume of the Drug 'B' is to be injected. Operation 1045 comprises associating a particular syringe (e.g., a syringe different from that used for transfer of Drug "A") with the medicine vial containing Drug "B", and transferring a volume of Drug "B" to the syringe similarly to Operation 915 described above. Operation 1050 comprises weighing and generating a database entry for the medicine vial following transfer of fluid to the syringe. Operation 1055 comprises associating the syringe containing the transferred volume of Drug "B" with the IV bag. This association may again be generated by the transfer monitoring unit 818, which may identify the syringe and the IV bag when the RF tag 18 carried by the syringe comes within sufficient proximity of the RF tag 48 carried by the IV bag when the needle 16 of the syringe is inserted into the membrane 42 of the injection port 40 of the IV bag. The transfer monitoring unit 818 may further update the database with an entry reflecting this association. Operation 1060 comprises weighing the IV bag following transfer of Drug "B" from the syringe to the IV bag and the transfer monitoring unit 818 generating a database entry reflecting the transfer of a volume of Drug "B" to the IV bag.

Thus, following completion of the steps of FIG. 10, the IV bag contains quantities of both Drug "A" and Drug "B." FIG. 11 illustrates a screenshot of a database illustrating a history of medications transferred to the IV bag following the steps of FIG. 10 according to an exemplary embodiment of the present invention. Accordingly, in exemplary embodiments, the transfer monitoring unit 818 is configured to generate and update a database storing entries for each individual fluid transfer that may occur during preparation of a dosage (e.g., a syringe dosage, IV dosage, and/or the like) so that it may later be verified. This fluid transfer history may illustrate an identity of each fluid reservoir (e.g., a medicine vial, IV bag, and/or the like) in association with an identity of a syringe used to transfer fluid to or from the fluid reservoir.

It will be appreciated that embodiments of the invention may be applied further downstream in administration of dosages as well as outside of a sterile pharmaceutical preparation environment. For example, the transfer monitoring unit 818 may further be configured to monitor transfer of fluid from initial preparation until it is transferred into an IV injection port, such as that illustrated in FIG. 7 at a patient's bedside. The transfer monitoring unit 818 may accordingly be configured to detect a transfer of fluid between a syringe and an IV injection port at bedside, due to a change in state emitted by one or more of the RF tag 18 and RF tag 59 when the needle 16 is inserted through the membrane 52. Other example fluid transfers that may be detected and tracked by the transfer monitoring unit 818 through detection of a change in state of an RF tag include, for example, association of an IV bag with an IV line port at a patient's bedside and association of a syringe with a syringe pump at bedside. Accordingly, an IV line port may carry an RF tag associated with the IV line port that may trigger a state change in an RF tag 48 when an IV bag is connected to the line port. Similarly, a syringe pump may carry an RF tag associated with the syringe pump that may trigger a state change in an RF tag 18 when the syringe is connected to the syringe pump.

FIG. 12 is a flowchart of a system, method, and computer program product according to exemplary embodiments of the invention. It will be understood that each block or step of the flowchart, and combinations of blocks in the flowchart, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices of and/or otherwise accessible to a computing device and executed by a processor in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the instructions of the computer program product which execute on the computer or other programmable apparatus create means for implementing the functions specified in the flowchart block(s) or step(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture including instruction means which implement the function specified in the flowchart block(s) or step(s). The computer program instructions of one or more computer program products may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart block(s) or step(s).

Accordingly, blocks or steps of the flowchart support combinations of means for performing the specified functions, combinations of steps for performing the specified functions and program instruction means for performing the specified functions. It will also be understood that one or more blocks or steps of the flowchart, and combinations of blocks or steps in the flowchart, may be implemented by special purpose hardware-based computer systems which perform the specified functions or steps, or combinations of special purpose hardware and computer instructions.

In this regard, one exemplary method for monitoring a transfer of fluid between a syringe 10 and a fluid reservoir (e.g., a medicine vial, IV bag, IV injection port, and/or the like) according to an exemplary embodiment of the present invention is illustrated in FIG. 12. The method includes the transfer monitoring unit 818 detecting a change in state of a signal emitted by at least one of a first signaling tag (e.g., RF tag 18) carried by the syringe 10 or a second signaling tag carried by a fluid reservoir, at operation 1200. This change in state is triggered by the first signaling tag coming within sufficient proximity of the second signaling tag when a needle of the syringe is inserted through a membrane of the fluid reservoir and may be indicative of a transfer of fluid between the syringe and the fluid reservoir. Operation 1210 comprises the transfer monitoring unit 818 determining an identity of the syringe based at least in part upon information carried by a signal emitted by the first signaling tag. Operation 1220 comprises the transfer monitoring unit 818 determining an identity of the fluid reservoir based at least in part upon information carried by a signal emitted by the second signaling tag. It will be appreciated, however, that the ordering of operations 1200-1220 is not important and may take place in an order other than that illustrated in FIG. 12 and described herein. Operation 1230 comprises the transfer monitoring unit 818 associating the syringe with the fluid reservoir based at least in part upon the determined identities. This association may be indicative that a transfer of fluid between the identified syringe and identified fluid reservoir occurred. Operation 1240 then comprises the transfer monitoring unit 818 storing an entry reflecting the association in a database.

The database may later be accessed to view a history of fluid transfer, such as for verifying medication dosages prior to administration.

The above described functions may be carried out in many ways. For example, any suitable means for carrying out each of the functions described above may be employed to carry out embodiments of the invention. In one embodiment, a suitably configured processor may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

As such, then, embodiments of the invention provide a syringe, such as may be used for transfer of fluid between a fluid reservoir and the syringe, which facilitates monitoring of the fluid transfer. Embodiments of the invention further provide a method and computer program product for monitoring a transfer of fluid between a syringe and fluid reservoir and generation of a database comprising a history of the transfer. The fluid transfer history may be used to verify preparation of medication dosages prior to administration and may reflect volumes of multiple medications transferred to a fluid reservoir, such as, for example, an IV bag.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A syringe comprising:
   a chamber for holding fluid transferred between the syringe and a fluid reservoir;
   a distal end comprising a point of attachment for a needle enabling transfer of fluid between the syringe and the fluid reservoir; and
   a first signaling tag carried by the syringe;
   wherein the first signaling tag is positioned such that when the needle is inserted through a membrane of the fluid reservoir for transferring fluid between the syringe and the fluid reservoir, the first signaling tag comes into a sufficient proximity with a second signaling tag carried by the fluid reservoir to trigger a change in state of a signal emitted by at least one of the first signaling tag or second signaling tag, wherein the change in state is indicative of an associative relationship between the syringe and the fluid reservoir.

2. A syringe according to claim 1, wherein:
   the first signaling tag comprises a radio frequency tag; and
   the second signaling tag comprises a radio frequency tag.

3. A syringe according to claim 1, wherein a signal emitted by the first signaling tag conveys information identifying the syringe and a signal emitted by the second signaling tag conveys information identifying the fluid reservoir.

4. A syringe according to claim 1, wherein:
   the first signaling tag comprises an antenna configured to become detuned when the first signaling tag is coupled to another signaling tag due to being in a sufficient proximity of the another signaling tag; and
   the change in state triggered when the first and second signaling tags come into a sufficient proximity comprises cessation of emission of a readable signal from the first signaling tag due to coupling of the first and second signaling tags.

5. A syringe according to claim 1, wherein:
   the first signaling tag comprises an antenna configured to be detuned when the first signaling tag is not within a sufficient proximity of the second signaling tag, wherein the antenna is further configured to be activated such that the secondary antenna emits a readable signal when the first signaling tag comes within a sufficient proximity of the second signaling tag when the needle is inserted through the membrane of the fluid reservoir; and
   the change in state triggered when the first and second signaling tags come into a sufficient proximity comprises emission of a readable signal from the antenna of the first signaling tag.

6. A syringe according to claim 1, wherein:
   the first signaling tag is configured to emit a first signal when the first signaling tag is not within a sufficient proximity of the second signaling tag and to emit a second signal when the first signaling tag comes within a sufficient proximity of the second signaling tag when the needle is inserted through a membrane of the fluid reservoir; and
   the change in state triggered when the first and second signaling tags come into a sufficient proximity comprises emission of the second signal from the first signaling tag.

7. A method for monitoring a transfer of fluid between a syringe and a fluid reservoir, wherein the syringe comprises a distal end providing a point of attachment for a needle enabling the transfer of fluid and the fluid reservoir comprises a membrane through which the needle is inserted for transferring fluid between the syringe and the fluid reservoir, the method comprising:
   detecting a change in state of a signal emitted by at least one of a first signaling tag carried by the syringe or a second signaling tag carried by the fluid reservoir, the change in state of the signal triggered as a result of the first and second signaling tags coming into a sufficient proximity of one another when the needle is inserted through the membrane, wherein the change in state of the signal is indicative of an associative relationship between the syringe and the fluid reservoir;
   determining an identity of the syringe based at least in part upon information carried by a signal emitted by the first signaling tag;
   determining an identity of the fluid reservoir based at least in part upon information carried by a signal emitted by the second signaling tag;

associating the syringe with the fluid reservoir based at least in part upon the determined identities; and storing an entry reflecting the association between the syringe and the fluid reservoir in a database.

8. A method according to claim 7, wherein:
the fluid reservoir comprises a medication vial containing medication; and
the transfer of fluid between the syringe and the fluid reservoir comprises transferring medication from the medication vial to the syringe.

9. A method according to claim 8, further comprising:
detecting a change in state of a signal emitted by at least one of the first signaling tag or a third signaling tag carried by a second fluid reservoir, the change in state of the signal emitted by at least one of the first signaling tag or the third signaling tag triggered as a result of the first and third signaling tags coming into a sufficient proximity of one another when the needle is inserted through a membrane of the second fluid reservoir, wherein the change in state of the signal emitted by at least one of the first signaling tag or the third signaling tag is indicative of the transfer of the medication from the syringe to the second fluid reservoir;
identifying the syringe based at least in part upon information carried by a signal emitted by the first signaling tag;
identifying the second fluid reservoir based at least in part upon information carried by a signal emitted by the third signaling tag;
associating the syringe with the second fluid reservoir, the association indicative that fluid was transferred from the syringe to the fluid reservoir; and
storing an entry reflecting the association between the syringe and the second fluid reservoir in the database so as to build a history of the medication transferred to the second fluid reservoir.

10. A method according to claim 9, wherein the second fluid reservoir comprises an intravenous bag or an intravenous line.

11. A method according to claim 8, further comprising:
determining a volume of medication in the medication vial prior to the transfer of medication from the medication vial to the syringe;
determining a volume of medication in the medication vial after the transfer of medication from the medication vial to the syringe; and
determining a volume of medication transferred to the syringe based at least in part upon the volume prior to the transfer and the volume after the transfer;
wherein storing an entry reflecting the association between the syringe and the fluid reservoir in a database further comprises storing an indication of the volume of medication transferred to the syringe.

12. A method according to claim 7, wherein storing an entry reflecting the association between the syringe and the fluid reservoir in a database further comprises storing a time stamp reflecting a time at which the transfer of fluid between the syringe and the fluid reservoir occurred.

13. A method according to claim 7, wherein
the first signaling tag comprises a radio frequency tag; and
the second signaling tag comprises a radio frequency tag.

14. A computer program product for monitoring a transfer of fluid between a syringe and a fluid reservoir, wherein the syringe comprises a distal end providing a point of attachment for a needle enabling the transfer of fluid and the fluid reservoir comprises a membrane through which the needle is inserted for transferring fluid between the syringe and the fluid reservoir; wherein the computer program product comprises at least one non-transitory computer-readable storage medium having computer-readable program instructions stored therein, the computer-readable program instructions comprising:
a program instruction for detecting a change in state of a signal emitted by at least one of a first signaling tag carried by the syringe or a second signaling tag carried by the fluid reservoir, the change in state of the signal triggered as a result of the first and second signaling tags coming into a sufficient proximity of one another when the needle is inserted through the membrane, wherein the change in state of the signal is indicative of an associative relationship between the syringe and the fluid reservoir;
a program instruction for determining an identity of the syringe based at least in part upon information carried by a signal emitted by the first signaling tag;
a program instruction for determining an identity of the fluid reservoir based at least in part upon information carried by a signal emitted by the second signaling tag;
a program instruction for associating the syringe with the fluid reservoir based at least in part upon the determined identities; and
a program instruction for storing an entry reflecting the association between the syringe and the fluid reservoir in a database.

15. A computer program product according to claim 14, wherein:
the fluid reservoir comprises a medication vial containing medication;
the transfer of fluid between the syringe and the fluid reservoir comprises transferring medication from the medication vial to the syringe; and
the program instruction for storing an entry comprises instructions for storing an entry reflecting that medication was transferred from the medication vial to the syringe.

16. A computer program product according to claim 15, further comprising:
a program instruction for detecting a change in state of a signal emitted by at least one of the first signaling tag or a third signaling tag carried by a second fluid reservoir, the change in state of the signal emitted by at least one of the first signaling tag or the third signaling tag triggered as a result of the first and third signaling tags coming into a sufficient proximity of one another when the needle is inserted through a membrane of the second fluid reservoir, wherein the change in state of the signal emitted by at least one of the first signaling tag or the third signaling tag is indicative of the transfer of the medication from the syringe to the second fluid reservoir;
a program instruction for identifying the syringe based at least in part upon information carried by a signal emitted by the first signaling tag;
a program instruction for identifying the second fluid reservoir based at least in part upon information carried by a signal emitted by the third signaling tag;
a program instruction for associating the syringe with the second fluid reservoir, the association indicative that fluid was transferred from the syringe to the fluid reservoir; and
a program instruction for storing an entry reflecting the association between the syringe and the second fluid reservoir in the database so as to build a history of the medication transferred to the second fluid reservoir.

17. A computer program product according to claim 16, wherein the second fluid reservoir comprises an intravenous bag or an intravenous line.

18. A computer program product according to claim 15, further comprising:
 a program instruction for determining a volume of medication in the medication vial prior to the transfer of medication from the medication vial to the syringe;
 a program instruction for determining a volume of medication in the medication vial after the transfer of medication from the medication vial to the syringe;
 a program instruction for determining a volume of medication transferred to the syringe based at least in part upon the volume prior to the transfer and the volume after the transfer; and
 wherein the program instruction for storing an entry reflecting the association between the syringe and the fluid reservoir in a database includes instructions for storing an indication of the volume of medication transferred to the syringe.

19. A computer program product according to claim 14, wherein the program instruction for storing an entry reflecting the association between the syringe and the fluid reservoir in a database further comprises instructions for storing a time stamp reflecting a time at which the transfer of fluid between the syringe and the fluid reservoir occurred.

20. A computer program product according to claim 14, wherein:
 the first signaling tag comprises a radio frequency tag; and
 the second signaling tag comprises a radio frequency tag.

21. A first fluid reservoir comprising:
 a first fluid transfer point; and
 a first signaling tag carried by the first fluid reservoir;
 wherein the first signaling tag is positioned such that when the first fluid transfer point comes into contact with a second fluid transfer point of a second fluid reservoir for transferring fluid between the first fluid reservoir and the second fluid reservoir, the first signaling tag comes into a sufficient proximity with a second signaling tag carried by the second fluid reservoir to trigger a change in state of a signal emitted by at least one of the first signaling tag or second signaling tag, wherein the change in state is indicative of an associative relationship between the first fluid reservoir and the second fluid reservoir and wherein the change in state is detectable by a tag reader that is positioned remotely from both the first fluid reservoir and the second fluid reservoir.

22. A first fluid reservoir according to claim 21, wherein the second fluid reservoir comprises a syringe.

23. A first fluid reservoir according to claim 21, wherein the first fluid reservoir comprises an intravenous bag and the second fluid reservoir comprises an intravenous line.

* * * * *